(12) United States Patent
Livingstone et al.

(10) Patent No.: US 7,906,297 B2
(45) Date of Patent: Mar. 15, 2011

(54) REAGENTS FOR THE DETECTION OF PHOSPHORYLATED ATR KINASE (SER 428) AND USES THEREOF

(75) Inventors: Mark Livingstone, Montreal (CA); Hong Ruan, Middleton, MA (US); Robert Polakiewicz, Lexington, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 946 days.

(21) Appl. No.: 11/487,883

(22) Filed: Jul. 17, 2006

(65) Prior Publication Data

US 2007/0166764 A1    Jul. 19, 2007

Related U.S. Application Data

(60) Provisional application No. 60/700,979, filed on Jul. 20, 2005.

(51) Int. Cl.
| | |
|---|---|
| C07K 16/18 | (2006.01) |
| C07K 16/40 | (2006.01) |
| G01N 33/53 | (2006.01) |
| G01N 33/536 | (2006.01) |
| G01N 33/543 | (2006.01) |
| G01N 33/573 | (2006.01) |
| G01N 33/577 | (2006.01) |
| C12P 21/08 | (2006.01) |

(52) U.S. Cl. ........ 435/7.4; 435/15; 435/70.21; 435/452; 435/194; 435/331; 435/338; 435/975; 436/518; 436/536; 436/547; 436/548; 530/387.1; 530/388.26; 530/389.1; 530/391.1; 530/391.3

(58) Field of Classification Search .................. 435/7.4, 435/15, 70.21, 452, 194, 331, 338, 975; 436/518, 436/536, 547, 548; 530/387.1, 388.26, 389.1, 530/391.1, 391.3
See application file for complete search history.

(56) References Cited

U.S. PATENT DOCUMENTS

| | | | |
|---|---|---|---|
| 6,441,140 | B1 | 8/2002 | Tan et al. |
| 7,259,022 | B2 | 8/2007 | Comb et al. |
| 2003/0068652 | A1 | 4/2003 | Zhang et al. |
| 2005/0037446 | A1 | 2/2005 | Schmitt et al. |

FOREIGN PATENT DOCUMENTS

| | | |
|---|---|---|
| WO | WO 93/21230 | 10/1993 |
| WO | WO 94/18324 | 9/1994 |

OTHER PUBLICATIONS

Czernik et al., 1991. Production of phosphorylation state-specific antibodies. Methods in Enzymology 201: 264-283.*
Keegan et al., 1996. The Atr and Atm protein kinases associate with different sites along meiotically pairing chromosomes. Genes & Development 10: 2423-2437.*
Yaffe et al., "A motif-based profile scanning approach for genome-wide prediction of signaling pathways" Nature Biotechnology 19(4): 348-53 (2001).
Songyang et al., "Use of an oriented peptide library to determine the optimal substrates of protein kinases" Current Biology 4: 973-982 (1994).
Songyang et al., "Catalytic specificity of protein-tyrosine kinases is critical for selective signaling" Nature 373: 536-539 (1995).
Cortez et al., "ATR and ATRIP: Partners in Checkpoint Signaling" Science 294: 1713-1716 (2001).
Casper et al., "Chromosomal Instability at Common Fragile Sites in Seckel Syndrome" Am. J. Hum. Genet. 75: 654-660 (2004).
Zou et al., "Sensing DNA Damage Through ATRIP Recognition of RPA-ssDNA Complexes" Science 300: 1542-1548 (2003).
Bao et al., "ATR/ATM-mediated phosphorylation of human Rad17 is required for genotoxic stress responses" Nature 411: 969-974 (2001).
Tibbetts et al., "A role for ATR in the DNA damage-induced Phosphorylation of p53" Genes & Development 13:152-157 (1999).
Gatei et al, "Ataxia Telangiecstasia Mutated (ATM Kinase and ATM Rad3 Related Kinase Mediate Phosphorylation of Brea1 at Distinct and Overlapping Sites" The Journal of Biological Chemistry 276 (20):17276-17280 (2001).
Internet citation: http://las.perkinelmer.com/Catalog/ProductInfoPage.htm?ProductID=AD0186 and http://las.perkinelmer.com/Catalog/COASearch.htm?CatalogNumber=AD0186, 2009.

* cited by examiner

*Primary Examiner* — Shafiqul Haq
*Assistant Examiner* — James L Grun
(74) *Attorney, Agent, or Firm* — Nancy Chiu Wilker

(57) ABSTRACT

The invention discloses two novel phosphorylation sites in human ATR kinase, serine 428 (Ser428) and serine 2317 (Ser2317) respectively, and provides reagents, including antibodies and AQUA peptides, that selectively bind to and/or detect ATR only when phosphorylated at one or more of these respective sites, but do not bind to ATR when not phosphorylated at these respective sites. Also provided are methods for determining the phosphorylation of ATR kinase in a biological sample, by using a detectable reagent that binds to ATR only when phosphorylated at Ser428 and/or Ser2317. Kits comprising the ATR (Ser428, Ser2317)-specific reagents of the invention are also provided.

6 Claims, 3 Drawing Sheets

Figure 1.

MGEHGLELASMIPALRELGSATPEEYNTVVQKPRQILCQFIDRILTDVNVVAVELVKKTD
SQPTSVMLLDFIQHIMKSSPLMFVNVSGSHEAKGSCIEFSNWIITRLLRIAATPSCHLLH
KKICEVICSLLFLFKSKSPAIFGVLTKELLQLFEDLVYLHRRNVMGHAVEWPVVMSRFLS
QLDEHMGYLQSAPLQLMSMQNLEFIEVTLLMVLTRIIAIVFFRRQELLLWQIGCVLLEYG
SPKIKSLAISFLTELFQLGGLPAQPASTFFSSFLELLKHLVEMDTDQLKLYEEPLSKLIK
TLFPFEAEAYRNIEPVYLNMLLEKLCVMFEDGVLMRLKSDLLKAALCHLLQYFLKFVPAG
YESALQVRKVYVRNICKALLDVLGIEVDAEYLLGPLYAALKMESMEIIEEIQCQTQQENL
SSNSDGISPKRRRLSSSLNPSKRAPKQTEEIKHVDMNQKSILWSALKQKAESLQISLEYS
GLKNPVIEMLEGIAVVLQLTALCTVHCSHQNMNCRTFKDCQHKSKKKPSVVITWMSLDFY
TKVLKSCRSLLESVQKLDLEATIDKVVKIYDALIYMQVNSSFEDHILEDLCGMLSLPWIY
SHSDDGCLKLTTFAANLLTLSCRISDSYSPQAQSRCVFLLTLFPRRIFLEWRTAVYNWAL
QSSHEVIRASCVSGFFILLQQQNSCNRVPKILIDKVKDDSDIVKKEFASILGQLVCTLHG
MFYLTSSLTEPFSEHGHVDLFCRNLKATSQHECSSSQLKASVCKPFLFLLKKKIPSPVKL
AFIDNLHHLCKHLDFREDETDVKAVLGTLLNLMEDPDKDVRVAFSGNIKHILESLDSEDG
FIKELFVLRMKEAYTHAQISRNNELKDTLILTTGDIGRAAKGDLVPFALLHLLHCLLSKS
ASVSGAAYTEIRALVAAKSVKLQSFFSQYKKPICQFLVESLHSSQMTALPNTPCQNADVR
KQDVAHQREMALNTLSEIANVFDFPDLNRFLTRTLQVLLPDLAAKASPAASALIRTLGKQ
LNVNRREILINNFKYIFSHLVCSCSKDELERALHYLKNETEIELGSLLRQDFQGLHNELL
LRIGEHYQQVFNGLSILASFASSDDPYQGPRDIISPELMADYLQPKLLGILAFFNMQLLS
SSVGIEDKKMALNSLMSLMKLMGPKHVSSVRVKMMTTLRTGLRFKDDFPELCCRAWDCFV
RCLDHACLGSLLSHVIVALLPLIHIQPKETAAIFHYLIIENRDAVQDFLHEIYFLPDHPE
LKKIKAVLQEYRKETSESTDLQTTLQLSMKAIQHENVDVRIHALTSLKETLYKNQEKLIK
YATDSETVEPIISQLVTVLLKGCQDANSQARLLCGECLGELGAIDPGRLDFSTTETQGKD
FTFVTGVEDSSFAYGLLMELTRAYLAYADNSRAQDSAAYAIQELLSIYDCREMETNGPGH
QLWRRFPEHVREILEPHLNTRYKSSQKSTDWSGVKKPIYLSKLGSNFAEWSASWAGYLIT
KVRHDLASKIFTCCSIMMKHDFKVTIYLLPHILVYVLLGCNQEDQQEVYAEIMAVLKHDD
QHTINTQDIASDLCQLSTQTVFSMLDHLTQWARHKFQALKAEKCPHSKSNRNKVDSMVST
VDYEDYQSVTRFLDLIPQDTLAVASFRSKAYTRAVMHFESFITEKKQNIQEHLGFLQKLY
AAMHEPDGVAGVSAIRKAEPSLKEQILEHESLGLLRDATACYDRAIQLEPDQIIHYHGVV
KSMLGLGQLSTVITQVNGVHANRSEWTDELNTYRVEAAWKLSQWDLVENYLAADGKSTTW
SVRLGQLLLSAKKRDITAFYDSLKLVRAEQIVPLSAASFERGSYQRGYEYIVRLHMLCEL
EHSIKPLFQHSPGDSSQEDSLNWVARLEMTQNSYRAKEPILALRRALLSLNKRPDYNEMV
GECWLQSARVARKAGHHQTAYNALLNAGESRLAELYVERAKWLWSKGDVHQALIVLQKGV
ELCFPENETPPEGKNMLIHGRAMLLVGRFMEETANFESNAIMKKYKDVTACLPEWEDGHF
YLAKYYDKLMPMVTDNKMEKQGDLIRYIVLHFGRSLQYGNQFIYQSMPRMLTLWLDYGTK
AYEWEKAGRSDRVQMRNDLGKINKVITEHTNYLAPYQFLTAFSQLISRICHSHDEVFVVL
MEIIAKVFLAYPQQAMWMMTAVSKSSYPMRVNRCKEILNKAIHMKKSLEKFVGDATRLTD
KLLELCNKPVDGSSSTLSMSTHFKMLKKLVEEATFSEILIPLQSVMIPTLPSILGTHANH
ASHEPFPGHWAYIAGFDDMVEILASLQKPKKISLKGSDGKFYIMMCKPKDDLRKDCRLME
FNSLINKCLRKDAESRRRELHIRTYAVIPLNDECGIIEWVNNTAGLRPILTKLYKEKGVY
MTGKELRQCMLPKSAALSEKLKVFREFLLPRHPPIFHEWFLRTFPDPTSWYSSRSAYCRS
TAVMSMVGYILGLGDRHGENILFDSLTGECVHVDFNCLFNKGETFEVPEIVPFRLTHNMV
NGMGPMGTEGLFRRACEVTMRLMRDQREPLMSVLKTFLHDPLVEWSKPVKGHSKAPLNET
GEVVNEKAKTHVLDIEQRLQGVIKTRNRVTGLPLSIEGHVHYLIQEATDENLLCQMYLGW
TPYM

Figure 2.

```
MGDHGLELASMIPALRELGSATPEEYNTVVQKPRQILCQFIDRILTDVNVVALELVKKTD
AQPTSVMLLDFIQHIMKSSPLMFVNVNGSQGQNEAKDSCIEFSHWIITRLLRIAATPSCH
MLHKKICEVICSLLFLFKSKNPAIFGVLTRELLYLFEDLIYLHKRNAVGEVMEWPVVVSR
FLSRLDEHMGCLQPAPLQFMNVQNVEFIEVTLLMVLIHIVPTVFFRRQELLLWQIGCALL
EHGSPKIRSLAISLLTELFELGGLPAQPASTFFSLFLELLQHLVGMDADQLKLYEEPLSK
LLKTLFPFEAEAYRNIEPVYLNVLLEKLSVMFEDRVLMRLKSDLLKAALCHLLQYFLTFV
PAGYESALQVRKVYVTNICRALVDALGVQKHVGYLLGPFYAALKMESKEIIERIQCQAQQ
ENLSGNNDEVSPKRRKLSSSLSSYKKPSRQPEEIIHVDMDKKSILWNVLKQKAESLQISL
ECGTLKNSVAEALEGITVVLQLTALCTVHCSHQDMDGHNVKDHQHKYKKKPPVVVTWMSL
DFYTKVLKSCRSLLESVQKLELELVIDSMVRICDALMYMQVKSSFKDHVLEELCGMLSLP
WIYSYSDDNSLKMTTFATNLLPLSQRVWDSYSPQAQSKCVFLLTLFPRRIFLEWRTAVYN
WALKSSHEVIRASCVKGFFILLHQQNSCNQIPKMLVDRVKDDSDMVKKEFASVLGQLVCT
LHGMFYLSSSVEPCFEHMDLFSKNLKATSQHECSSSQVKASTCKPFLFLLTKNTPSPVKL
AFIDNLHHLCKHLDFQEDEREVKAVLGTLLNLMEDPDKDVRIAFSGNIKYILESLNSEDG
FVKELFVLRMKEAYTHAQIARNNELKDTLILTTGDIGRAAKGDLIPFALLHLLHCLLSKS
ASVSGAAYTEIRALVAAKSVKLQNFFSQYKKPICQFLVESLHSSQMTALPSAPCQSSEIR
KQDVAHHREMALNTLSEIANVFDFPDLNRFLTRTLQVLLPDLAAKASPAASALIRTLGKQ
LNVSRREILINNFKYIFSHLVCSCSKDELERALHYLKNETEIELGSLLRQDFQGLHNELL
LRIGEHYQQVFNGLSILASFASSDDPYQGPRDITSPELMADYLQPKLLGILAFFNMQLLS
SSVGIEDKKMALTSLMSLMKLMGPKHVSSVRVKMMTTLRTGLRFKDDFPELCCRAWDCFV
RCLDHAYLGPLLSHVIVALLPLIHMQPKETAAIFHYLIIENRDAVQDFLHEIYFLPDHPE
LEKIKAVLQEYRKETSETTDLQTTLQLSMKAIQHENVDVRIHALTSLKETLYKNQEKLIK
YATDSETVEPVISQLVTVILKGCQDANSQARLLCGECLGELGAIDPGRLDFSTTETQGKD
FTFVTGVEDLSFAYGLLMELTRAYLAYADNSRAQDSAAYAIQELLSIYDCREMQSNGPGY
QLWKRFPEHVREILEPHLNTRYKSSQKSTDWSGVTKPIYLSKLGNNFAEWSSSWAGYLIT
KVRDNLASKIFTCCSIMMKHDFKVTIYLLPHILVYVLLGCNQEDQQEVYAEIMAVLKHDE
QHAISTQDSASDLCQLSTQTVFSVLDHLTQWARHKFQALNAEKLAQNKPKGVSNVNFEDY
QSVTRFLDLIPQDTLAVASFRSKAYTRAVMHFESFITEKKQNIQKHLGFLQKLYAAMHEP
DGVAGVSAIRKAEPSLKEQILEHESIGLLRDATACYDRAIQLEPDQIIHYGVVKSMLGL
GQLSTVITQVNGVHANRSEWTDELNTYRVEAAWKLSQWDLVENYLAADGKSTTWSVRLGQ
LLLSAKKRDTTTFYDTLKLVRAEQIVPLSAASFERGSYQRGYEFIVRLHMLCELEHSLKP
LFRKSPGDSCNEDSLNWGARLEMTQNSYRAKEPILALRRALLSLNKRPDYNEMVGECWLQ
SARVARKAGHHQTAYNALLNAGESRLAELYVERAKWLWSKGDVHQALIVLQKGVELCFPE
NKSPSESKHMLIHGRATLLVGRFMEETANFESNAVMKKYKDVTLFLPEWEDGHFYLAKYY
DKLMPMVTDNKMEKQGDLIRYIVLHFGRSLQYGNQFIYQSMPRMLSLWLDFGAKAYEWEK
GGRSDRLQMRNDLAKINSVLTEHTNRLAPYQFLTAFSQLISRICHSHDEVFVVLMEIIAK
VFLAYPQQAMWMMTAVSKSSYPMRVNRCKEILTKAIHMKKSLEKFVGDATRLTDKLLELC
NKSVDGSNSTLSMSTHFKMLKRLVEDPTFSEILIPLQSVMIPTLPSVLGAHANHDPFPGH
WAYLAGFDDVVEILSSLQKPKKISLKGSDGKFYIMMCKPKDDLRKDCRLMEFNSLINKSL
RKDAESRRRELHIRTYAVIPLNDECGIIEWVNNTAGLRPILTKIYKEKGVYMTGKELRQC
MLPKSAALSEKLKVFQELLLPRHPPVFHEWFLRTFPDPTSWYSSRSAYCRSTAVMSMVGY
ILGLGDRHGENILFDSFTGECVHVDFNCLFNKGETFEVPEIVPFRLTHNMVNGMGPMGTE
GLFRRACEVTLRLMRDQREPLMSVLKTFLHDPLVEGSKPVKGHSKAPLNETGEVVNEKAK
THVLDIEQRLQGVIKTRNRVTGLPLSIEGHVHYLIQEATDENLLCQMYLGWTPYM
```

1: Raw264.7 cells (Untreated)
2: Raw264.7 cells (UV-treated: 50mJ/cm$^2$, 30-minute recovery)
3: Raw264.7 cells (Nocodazole-treated: (50ng/ml, 16 hours)

SEQUENCE LISTING

```
<160> NUMBER OF SEQ ID NOS: 8

<210> SEQ ID NO 1
<211> LENGTH: 2644
<212> TYPE: PRT
<213> ORGANISM: Homo sapiens

<400> SEQUENCE: 1

Met Gly Glu His Gly Leu Glu Leu Ala Ser Met Ile Pro Ala Leu Arg
1               5                   10                  15

Glu Leu Gly Ser Ala Thr Pro Glu Glu Tyr Asn Thr Val Val Gln Lys
            20                  25                  30
```

-continued

```
Pro Arg Gln Ile Leu Cys Gln Phe Ile Asp Arg Ile Leu Thr Asp Val
        35                  40                  45
Asn Val Val Ala Val Glu Leu Val Lys Lys Thr Asp Ser Gln Pro Thr
 50                  55                  60
Ser Val Met Leu Leu Asp Phe Ile Gln His Ile Met Lys Ser Ser Pro
 65                  70                  75                  80
Leu Met Phe Val Asn Val Ser Gly Ser His Glu Ala Lys Gly Ser Cys
                 85                  90                  95
Ile Glu Phe Ser Asn Trp Ile Ile Thr Arg Leu Leu Arg Ile Ala Ala
                100                 105                 110
Thr Pro Ser Cys His Leu Leu His Lys Lys Ile Cys Glu Val Ile Cys
            115                 120                 125
Ser Leu Leu Phe Leu Phe Lys Ser Lys Ser Pro Ala Ile Phe Gly Val
        130                 135                 140
Leu Thr Lys Glu Leu Leu Gln Leu Phe Glu Asp Leu Val Tyr Leu His
145                 150                 155                 160
Arg Arg Asn Val Met Gly His Ala Val Glu Trp Pro Val Met Ser
                165                 170                 175
Arg Phe Leu Ser Gln Leu Asp Glu His Met Gly Tyr Leu Gln Ser Ala
            180                 185                 190
Pro Leu Gln Leu Met Ser Met Gln Asn Leu Glu Phe Ile Glu Val Thr
        195                 200                 205
Leu Leu Met Val Leu Thr Arg Ile Ile Ala Ile Val Phe Phe Arg Arg
210                 215                 220
Gln Glu Leu Leu Leu Trp Gln Ile Gly Cys Val Leu Leu Glu Tyr Gly
225                 230                 235                 240
Ser Pro Lys Ile Lys Ser Leu Ala Ile Ser Phe Leu Thr Glu Leu Phe
                245                 250                 255
Gln Leu Gly Gly Leu Pro Ala Gln Pro Ala Ser Thr Phe Phe Ser Ser
            260                 265                 270
Phe Leu Glu Leu Leu Lys His Leu Val Glu Met Asp Thr Asp Gln Leu
        275                 280                 285
Lys Leu Tyr Glu Glu Pro Leu Ser Lys Leu Ile Lys Thr Leu Phe Pro
290                 295                 300
Phe Glu Ala Glu Ala Tyr Arg Asn Ile Glu Pro Val Tyr Leu Asn Met
305                 310                 315                 320
Leu Leu Glu Lys Leu Cys Val Met Phe Glu Asp Gly Val Leu Met Arg
                325                 330                 335
Leu Lys Ser Asp Leu Leu Lys Ala Ala Leu Cys His Leu Leu Gln Tyr
            340                 345                 350
Phe Leu Lys Phe Val Pro Ala Gly Tyr Glu Ser Ala Leu Gln Val Arg
        355                 360                 365
Lys Val Tyr Val Arg Asn Ile Cys Lys Ala Leu Leu Asp Val Leu Gly
370                 375                 380
Ile Glu Val Asp Ala Glu Tyr Leu Leu Gly Pro Leu Tyr Ala Ala Leu
385                 390                 395                 400
Lys Met Glu Ser Met Glu Ile Ile Glu Glu Ile Gln Cys Gln Thr Gln
                405                 410                 415
Gln Glu Asn Leu Ser Ser Asn Ser Asp Gly Ile Ser Pro Lys Arg Arg
            420                 425                 430
Arg Leu Ser Ser Ser Leu Asn Pro Ser Lys Arg Ala Pro Lys Gln Thr
        435                 440                 445
Glu Glu Ile Lys His Val Asp Met Asn Gln Lys Ser Ile Leu Trp Ser
450                 455                 460
```

-continued

```
Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
            485                 490                 495

Leu Gln Leu Thr Ala Leu Cys Thr Val His Cys Ser His Gln Asn Met
        500                 505                 510

Asn Cys Arg Thr Phe Lys Asp Cys Gln His Lys Ser Lys Lys Lys Pro
    515                 520                 525

Ser Val Val Ile Thr Trp Met Ser Leu Asp Phe Tyr Thr Lys Val Leu
530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
            565                 570                 575

Gln Val Asn Ser Ser Phe Glu Asp His Ile Leu Glu Asp Leu Cys Gly
        580                 585                 590

Met Leu Ser Leu Pro Trp Ile Tyr Ser His Ser Asp Asp Gly Cys Leu
    595                 600                 605

Lys Leu Thr Thr Phe Ala Ala Asn Leu Leu Thr Leu Ser Cys Arg Ile
610                 615                 620

Ser Asp Ser Tyr Ser Pro Gln Ala Gln Ser Arg Cys Val Phe Leu Leu
625                 630                 635                 640

Thr Leu Phe Pro Arg Arg Ile Phe Leu Glu Trp Arg Thr Ala Val Tyr
            645                 650                 655

Asn Trp Ala Leu Gln Ser Ser His Glu Val Ile Arg Ala Ser Cys Val
        660                 665                 670

Ser Gly Phe Phe Ile Leu Leu Gln Gln Gln Asn Ser Cys Asn Arg Val
    675                 680                 685

Pro Lys Ile Leu Ile Asp Lys Val Lys Asp Asp Ser Asp Ile Val Lys
690                 695                 700

Lys Glu Phe Ala Ser Ile Leu Gly Gln Leu Val Cys Thr Leu His Gly
705                 710                 715                 720

Met Phe Tyr Leu Thr Ser Ser Leu Thr Glu Pro Phe Ser Glu His Gly
            725                 730                 735

His Val Asp Leu Phe Cys Arg Asn Leu Lys Ala Thr Ser Gln His Glu
        740                 745                 750

Cys Ser Ser Ser Gln Leu Lys Ala Ser Val Cys Lys Pro Phe Leu Phe
    755                 760                 765

Leu Leu Lys Lys Lys Ile Pro Ser Pro Val Lys Leu Ala Phe Ile Asp
770                 775                 780

Asn Leu His His Leu Cys Lys His Leu Asp Phe Arg Glu Asp Glu Thr
785                 790                 795                 800

Asp Val Lys Ala Val Leu Gly Thr Leu Leu Asn Leu Met Glu Asp Pro
            805                 810                 815

Asp Lys Asp Val Arg Val Ala Phe Ser Gly Asn Ile Lys His Ile Leu
        820                 825                 830

Glu Ser Leu Asp Ser Glu Asp Gly Phe Ile Lys Glu Leu Phe Val Leu
    835                 840                 845

Arg Met Lys Glu Ala Tyr Thr His Ala Gln Ile Ser Arg Asn Asn Glu
850                 855                 860

Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu Leu His Cys Leu
```

-continued

```
                885                 890                 895
Leu Ser Lys Ser Ala Ser Val Ser Gly Ala Ala Tyr Thr Glu Ile Arg
            900                 905                 910

Ala Leu Val Ala Ala Lys Ser Val Lys Leu Gln Ser Phe Phe Ser Gln
            915                 920                 925

Tyr Lys Lys Pro Ile Cys Gln Phe Leu Val Glu Ser Leu His Ser Ser
            930                 935                 940

Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
                965                 970                 975

Glu Ile Ala Asn Val Phe Asp Phe Pro Asp Leu Asn Arg Phe Leu Thr
            980                 985                 990

Arg Thr Leu Gln Val Leu Leu Pro Asp Leu Ala Ala Lys Ala Ser Pro
            995                 1000                1005

Ala Ala Ser Ala Leu Ile Arg Thr Leu Gly Lys Gln Leu Asn Val
        1010                1015                1020

Asn Arg Arg Glu Ile Leu Ile Asn Asn Phe Lys Tyr Ile Phe Ser
        1025                1030                1035

His Leu Val Cys Ser Cys Ser Lys Asp Glu Leu Glu Arg Ala Leu
        1040                1045                1050

His Tyr Leu Lys Asn Glu Thr Glu Ile Glu Leu Gly Ser Leu Leu
        1055                1060                1065

Arg Gln Asp Phe Gln Gly Leu His Asn Glu Leu Leu Leu Arg Ile
        1070                1075                1080

Gly Glu His Tyr Gln Gln Val Phe Asn Gly Leu Ser Ile Leu Ala
        1085                1090                1095

Ser Phe Ala Ser Ser Asp Asp Pro Tyr Gln Gly Pro Arg Asp Ile
        1100                1105                1110

Ile Ser Pro Glu Leu Met Ala Asp Tyr Leu Gln Pro Lys Leu Leu
        1115                1120                1125

Gly Ile Leu Ala Phe Phe Asn Met Gln Leu Leu Ser Ser Ser Val
        1130                1135                1140

Gly Ile Glu Asp Lys Lys Met Ala Leu Asn Ser Leu Met Ser Leu
        1145                1150                1155

Met Lys Leu Met Gly Pro Lys His Val Ser Ser Val Arg Val Lys
        1160                1165                1170

Met Met Thr Thr Leu Arg Thr Gly Leu Arg Phe Lys Asp Asp Phe
        1175                1180                1185

Pro Glu Leu Cys Cys Arg Ala Trp Asp Cys Phe Val Arg Cys Leu
        1190                1195                1200

Asp His Ala Cys Leu Gly Ser Leu Leu Ser His Val Ile Val Ala
        1205                1210                1215

Leu Leu Pro Leu Ile His Ile Gln Pro Lys Glu Thr Ala Ala Ile
        1220                1225                1230

Phe His Tyr Leu Ile Ile Glu Asn Arg Asp Ala Val Gln Asp Phe
        1235                1240                1245

Leu His Glu Ile Tyr Phe Leu Pro Asp His Pro Glu Leu Lys Lys
        1250                1255                1260

Ile Lys Ala Val Leu Gln Glu Tyr Arg Lys Glu Thr Ser Glu Ser
        1265                1270                1275

Thr Asp Leu Gln Thr Thr Leu Gln Leu Ser Met Lys Ala Ile Gln
        1280                1285                1290
```

-continued

His Glu Asn Val Asp Val Arg Ile His Ala Leu Thr Ser Leu Lys
1295                1300                1305

Glu Thr Leu Tyr Lys Asn Gln Glu Lys Leu Ile Lys Tyr Ala Thr
1310                1315                1320

Asp Ser Glu Thr Val Glu Pro Ile Ile Ser Gln Leu Val Thr Val
1325                1330                1335

Leu Leu Lys Gly Cys Gln Asp Ala Asn Ser Gln Ala Arg Leu Leu
1340                1345                1350

Cys Gly Glu Cys Leu Gly Glu Leu Gly Ala Ile Asp Pro Gly Arg
1355                1360                1365

Leu Asp Phe Ser Thr Thr Glu Thr Gln Gly Lys Asp Phe Thr Phe
1370                1375                1380

Val Thr Gly Val Glu Asp Ser Ser Phe Ala Tyr Gly Leu Leu Met
1385                1390                1395

Glu Leu Thr Arg Ala Tyr Leu Ala Tyr Ala Asp Asn Ser Arg Ala
1400                1405                1410

Gln Asp Ser Ala Ala Tyr Ala Ile Gln Glu Leu Leu Ser Ile Tyr
1415                1420                1425

Asp Cys Arg Glu Met Glu Thr Asn Gly Pro Gly His Gln Leu Trp
1430                1435                1440

Arg Arg Phe Pro Glu His Val Arg Glu Ile Leu Glu Pro His Leu
1445                1450                1455

Asn Thr Arg Tyr Lys Ser Ser Gln Lys Ser Thr Asp Trp Ser Gly
1460                1465                1470

Val Lys Lys Pro Ile Tyr Leu Ser Lys Leu Gly Ser Asn Phe Ala
1475                1480                1485

Glu Trp Ser Ala Ser Trp Ala Gly Tyr Leu Ile Thr Lys Val Arg
1490                1495                1500

His Asp Leu Ala Ser Lys Ile Phe Thr Cys Cys Ser Ile Met Met
1505                1510                1515

Lys His Asp Phe Lys Val Thr Ile Tyr Leu Leu Pro His Ile Leu
1520                1525                1530

Val Tyr Val Leu Leu Gly Cys Asn Gln Glu Asp Gln Gln Glu Val
1535                1540                1545

Tyr Ala Glu Ile Met Ala Val Leu Lys His Asp Asp Gln His Thr
1550                1555                1560

Ile Asn Thr Gln Asp Ile Ala Ser Asp Leu Cys Gln Leu Ser Thr
1565                1570                1575

Gln Thr Val Phe Ser Met Leu Asp His Leu Thr Gln Trp Ala Arg
1580                1585                1590

His Lys Phe Gln Ala Leu Lys Ala Glu Lys Cys Pro His Ser Lys
1595                1600                1605

Ser Asn Arg Asn Lys Val Asp Ser Met Val Ser Thr Val Asp Tyr
1610                1615                1620

Glu Asp Tyr Gln Ser Val Thr Arg Phe Leu Asp Leu Ile Pro Gln
1625                1630                1635

Asp Thr Leu Ala Val Ala Ser Phe Arg Ser Lys Ala Tyr Thr Arg
1640                1645                1650

Ala Val Met His Phe Glu Ser Phe Ile Thr Glu Lys Lys Gln Asn
1655                1660                1665

Ile Gln Glu His Leu Gly Phe Leu Gln Lys Leu Tyr Ala Ala Met
1670                1675                1680

His Glu Pro Asp Gly Val Ala Gly Val Ser Ala Ile Arg Lys Ala
1685                1690                1695

```
Glu Pro Ser Leu Lys Glu Gln Ile Leu Glu His Glu Ser Leu Gly
    1700                1705                1710

Leu Leu Arg Asp Ala Thr Ala Cys Tyr Asp Arg Ala Ile Gln Leu
    1715                1720                1725

Glu Pro Asp Gln Ile Ile His Tyr His Gly Val Val Lys Ser Met
    1730                1735                1740

Leu Gly Leu Gly Gln Leu Ser Thr Val Ile Thr Gln Val Asn Gly
    1745                1750                1755

Val His Ala Asn Arg Ser Glu Trp Thr Asp Glu Leu Asn Thr Tyr
    1760                1765                1770

Arg Val Glu Ala Ala Trp Lys Leu Ser Gln Trp Asp Leu Val Glu
    1775                1780                1785

Asn Tyr Leu Ala Ala Asp Gly Lys Ser Thr Thr Trp Ser Val Arg
    1790                1795                1800

Leu Gly Gln Leu Leu Leu Ser Ala Lys Lys Arg Asp Ile Thr Ala
    1805                1810                1815

Phe Tyr Asp Ser Leu Lys Leu Val Arg Ala Glu Gln Ile Val Pro
    1820                1825                1830

Leu Ser Ala Ala Ser Phe Glu Arg Gly Ser Tyr Gln Arg Gly Tyr
    1835                1840                1845

Glu Tyr Ile Val Arg Leu His Met Leu Cys Glu Leu Glu His Ser
    1850                1855                1860

Ile Lys Pro Leu Phe Gln His Ser Pro Gly Asp Ser Ser Gln Glu
    1865                1870                1875

Asp Ser Leu Asn Trp Val Ala Arg Leu Glu Met Thr Gln Asn Ser
    1880                1885                1890

Tyr Arg Ala Lys Glu Pro Ile Leu Ala Leu Arg Arg Ala Leu Leu
    1895                1900                1905

Ser Leu Asn Lys Arg Pro Asp Tyr Asn Glu Met Val Gly Glu Cys
    1910                1915                1920

Trp Leu Gln Ser Ala Arg Val Ala Arg Lys Ala Gly His His Gln
    1925                1930                1935

Thr Ala Tyr Asn Ala Leu Leu Asn Ala Gly Glu Ser Arg Leu Ala
    1940                1945                1950

Glu Leu Tyr Val Glu Arg Ala Lys Trp Leu Trp Ser Lys Gly Asp
    1955                1960                1965

Val His Gln Ala Leu Ile Val Leu Gln Lys Gly Val Glu Leu Cys
    1970                1975                1980

Phe Pro Glu Asn Glu Thr Pro Pro Glu Gly Lys Asn Met Leu Ile
    1985                1990                1995

His Gly Arg Ala Met Leu Leu Val Gly Arg Phe Met Glu Glu Thr
    2000                2005                2010

Ala Asn Phe Glu Ser Asn Ala Ile Met Lys Lys Tyr Lys Asp Val
    2015                2020                2025

Thr Ala Cys Leu Pro Glu Trp Glu Asp Gly His Phe Tyr Leu Ala
    2030                2035                2040

Lys Tyr Tyr Asp Lys Leu Met Pro Met Val Thr Asp Asn Lys Met
    2045                2050                2055

Glu Lys Gln Gly Asp Leu Ile Arg Tyr Ile Val Leu His Phe Gly
    2060                2065                2070

Arg Ser Leu Gln Tyr Gly Asn Gln Phe Ile Tyr Gln Ser Met Pro
    2075                2080                2085

Arg Met Leu Thr Leu Trp Leu Asp Tyr Gly Thr Lys Ala Tyr Glu
```

-continued

```
             2090                2095                2100

Trp Glu Lys Ala Gly Arg Ser Asp Arg Val Gln Met Arg Asn Asp
        2105                2110                2115

Leu Gly Lys Ile Asn Lys Val Ile Thr Glu His Thr Asn Tyr Leu
        2120                2125                2130

Ala Pro Tyr Gln Phe Leu Thr Ala Phe Ser Gln Leu Ile Ser Arg
        2135                2140                2145

Ile Cys His Ser His Asp Glu Val Phe Val Val Leu Met Glu Ile
        2150                2155                2160

Ile Ala Lys Val Phe Leu Ala Tyr Pro Gln Gln Ala Met Trp Met
        2165                2170                2175

Met Thr Ala Val Ser Lys Ser Ser Tyr Pro Met Arg Val Asn Arg
        2180                2185                2190

Cys Lys Glu Ile Leu Asn Lys Ala Ile His Met Lys Lys Ser Leu
        2195                2200                2205

Glu Lys Phe Val Gly Asp Ala Thr Arg Leu Thr Asp Lys Leu Leu
        2210                2215                2220

Glu Leu Cys Asn Lys Pro Val Asp Gly Ser Ser Ser Thr Leu Ser
        2225                2230                2235

Met Ser Thr His Phe Lys Met Leu Lys Lys Leu Val Glu Glu Ala
        2240                2245                2250

Thr Phe Ser Glu Ile Leu Ile Pro Leu Gln Ser Val Met Ile Pro
        2255                2260                2265

Thr Leu Pro Ser Ile Leu Gly Thr His Ala Asn His Ala Ser His
        2270                2275                2280

Glu Pro Phe Pro Gly His Trp Ala Tyr Ile Ala Gly Phe Asp Asp
        2285                2290                2295

Met Val Glu Ile Leu Ala Ser Leu Gln Lys Pro Lys Lys Ile Ser
        2300                2305                2310

Leu Lys Gly Ser Asp Gly Lys Phe Tyr Ile Met Met Cys Lys Pro
        2315                2320                2325

Lys Asp Asp Leu Arg Lys Asp Cys Arg Leu Met Glu Phe Asn Ser
        2330                2335                2340

Leu Ile Asn Lys Cys Leu Arg Lys Asp Ala Glu Ser Arg Arg Arg
        2345                2350                2355

Glu Leu His Ile Arg Thr Tyr Ala Val Ile Pro Leu Asn Asp Glu
        2360                2365                2370

Cys Gly Ile Ile Glu Trp Val Asn Asn Thr Ala Gly Leu Arg Pro
        2375                2380                2385

Ile Leu Thr Lys Leu Tyr Lys Glu Lys Gly Val Tyr Met Thr Gly
        2390                2395                2400

Lys Glu Leu Arg Gln Cys Met Leu Pro Lys Ser Ala Ala Leu Ser
        2405                2410                2415

Glu Lys Leu Lys Val Phe Arg Glu Phe Leu Leu Pro Arg His Pro
        2420                2425                2430

Pro Ile Phe His Glu Trp Phe Leu Arg Thr Phe Pro Asp Pro Thr
        2435                2440                2445

Ser Trp Tyr Ser Ser Arg Ser Ala Tyr Cys Arg Ser Thr Ala Val
        2450                2455                2460

Met Ser Met Val Gly Tyr Ile Leu Gly Leu Gly Asp Arg His Gly
        2465                2470                2475

Glu Asn Ile Leu Phe Asp Ser Leu Thr Gly Glu Cys Val His Val
        2480                2485                2490
```

```
Asp Phe Asn Cys Leu Phe Asn Lys Gly Glu Thr Phe Glu Val Pro
    2495                2500                2505

Glu Ile Val Pro Phe Arg Leu Thr His Asn Met Val Asn Gly Met
2510                2515                2520

Gly Pro Met Gly Thr Glu Gly Leu Phe Arg Arg Ala Cys Glu Val
    2525                2530                2535

Thr Met Arg Leu Met Arg Asp Gln Arg Glu Pro Leu Met Ser Val
2540                2545                2550

Leu Lys Thr Phe Leu His Asp Pro Leu Val Glu Trp Ser Lys Pro
    2555                2560                2565

Val Lys Gly His Ser Lys Ala Pro Leu Asn Glu Thr Gly Glu Val
2570                2575                2580

Val Asn Glu Lys Ala Lys Thr His Val Leu Asp Ile Glu Gln Arg
    2585                2590                2595

Leu Gln Gly Val Ile Lys Arg Asn Arg Val Thr Gly Leu Pro
2600                2605                2610

Leu Ser Ile Glu Gly His Val His Tyr Leu Ile Gln Glu Ala Thr
    2615                2620                2625

Asp Glu Asn Leu Leu Cys Gln Met Tyr Leu Gly Trp Thr Pro Tyr
2630                2635                2640

Met
```

<210> SEQ ID NO 2
<211> LENGTH: 2644
<212> TYPE: PRT
<213> ORGANISM: Mus musculus

<400> SEQUENCE: 2

```
Met Gly Glu His Gly Leu Glu Leu Ala Ser Met Ile Pro Ala Leu Arg
1               5                   10                  15

Glu Leu Gly Ser Ala Thr Pro Glu Glu Tyr Asn Thr Val Val Gln Lys
            20                  25                  30

Pro Arg Gln Ile Leu Cys Gln Phe Ile Asp Arg Ile Leu Thr Asp Val
        35                  40                  45

Asn Val Val Ala Val Glu Leu Val Lys Lys Thr Asp Ser Gln Pro Thr
    50                  55                  60

Ser Val Met Leu Leu Asp Phe Ile Gln His Ile Met Lys Ser Ser Pro
65                  70                  75                  80

Leu Met Phe Val Asn Val Ser Gly Ser His Glu Ala Lys Gly Ser Cys
                85                  90                  95

Ile Glu Phe Ser Asn Trp Ile Ile Thr Arg Leu Leu Arg Ile Ala Ala
            100                 105                 110

Thr Pro Ser Cys His Leu Leu His Lys Lys Ile Cys Glu Val Ile Cys
        115                 120                 125

Ser Leu Leu Phe Leu Phe Lys Ser Lys Ser Pro Ala Ile Phe Gly Val
    130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                165                 170                 175

Arg Phe Leu Ser Gln Leu Asp Glu His Met Gly Tyr Leu Gln Ser Ala
            180                 185                 190

Pro Leu Gln Leu Met Ser Met Gln Asn Leu Glu Phe Ile Glu Val Thr
        195                 200                 205

Leu Leu Met Val Leu Thr Arg Ile Ile Ala Ile Val Phe Phe Arg Arg
```

-continued

```
            210                 215                 220
Gln Glu Leu Leu Leu Trp Gln Ile Gly Cys Val Leu Leu Glu Tyr Gly
225                 230                 235                 240

Ser Pro Lys Ile Lys Ser Leu Ala Ile Ser Phe Leu Thr Glu Leu Phe
                245                 250                 255

Gln Leu Gly Gly Leu Pro Ala Gln Pro Ala Ser Thr Phe Phe Ser Ser
                260                 265                 270

Phe Leu Glu Leu Lys His Leu Val Glu Met Asp Thr Asp Gln Leu
            275                 280                 285

Lys Leu Tyr Glu Glu Pro Leu Ser Lys Leu Ile Lys Thr Leu Phe Pro
            290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                325                 330                 335

Leu Lys Ser Asp Leu Leu Lys Ala Ala Leu Cys His Leu Leu Gln Tyr
                340                 345                 350

Phe Leu Lys Phe Val Pro Ala Gly Tyr Glu Ser Ala Leu Gln Val Arg
                355                 360                 365

Lys Val Tyr Val Arg Asn Ile Cys Lys Ala Leu Leu Asp Val Leu Gly
            370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Glu Ile Gln Cys Gln Thr Gln
                405                 410                 415

Gln Glu Asn Leu Ser Ser Asn Ser Asp Gly Ile Ser Pro Lys Arg Arg
                420                 425                 430

Arg Leu Ser Ser Ser Leu Asn Pro Ser Lys Arg Ala Pro Lys Gln Thr
            435                 440                 445

Glu Glu Ile Lys His Val Asp Met Asn Gln Lys Ser Ile Leu Trp Ser
            450                 455                 460

Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
                485                 490                 495

Leu Gln Leu Thr Ala Leu Cys Thr Val His Cys Ser His Gln Asn Met
            500                 505                 510

Asn Cys Arg Thr Phe Lys Asp Cys Gln His Lys Ser Lys Lys Lys Pro
            515                 520                 525

Ser Val Val Ile Thr Trp Met Ser Leu Asp Phe Tyr Thr Lys Val Leu
            530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
                565                 570                 575

Gln Val Asn Ser Ser Phe Glu Asp His Ile Leu Glu Asp Leu Cys Gly
                580                 585                 590

Met Leu Ser Leu Pro Trp Ile Tyr Ser His Ser Asp Asp Gly Cys Leu
            595                 600                 605

Lys Leu Thr Thr Phe Ala Ala Asn Leu Leu Thr Leu Ser Cys Arg Ile
            610                 615                 620

Ser Asp Ser Tyr Ser Pro Gln Ala Gln Ser Arg Cys Val Phe Leu Leu
625                 630                 635                 640
```

-continued

```
Thr Leu Phe Pro Arg Arg Ile Phe Leu Glu Trp Arg Thr Ala Val Tyr
                645                 650                 655

Asn Trp Ala Leu Gln Ser Ser His Glu Val Ile Arg Ala Ser Cys Val
                660                 665                 670

Ser Gly Phe Phe Ile Leu Leu Gln Gln Gln Asn Ser Cys Asn Arg Val
                675                 680                 685

Pro Lys Ile Leu Ile Asp Lys Val Lys Asp Ser Asp Ile Val Lys
            690                 695                 700

Lys Glu Phe Ala Ser Ile Leu Gly Gln Leu Val Cys Thr Leu His Gly
705                 710                 715                 720

Met Phe Tyr Leu Thr Ser Ser Leu Thr Glu Pro Phe Ser Glu His Gly
                725                 730                 735

His Val Asp Leu Phe Cys Arg Asn Leu Lys Ala Thr Ser Gln His Glu
                740                 745                 750

Cys Ser Ser Ser Gln Leu Lys Ala Ser Val Cys Lys Pro Phe Leu Phe
                755                 760                 765

Leu Leu Lys Lys Lys Ile Pro Ser Pro Val Lys Leu Ala Phe Ile Asp
            770                 775                 780

Asn Leu His His Leu Cys Lys His Leu Asp Phe Arg Glu Asp Glu Thr
785                 790                 795                 800

Asp Val Lys Ala Val Leu Gly Thr Leu Asn Leu Met Glu Asp Pro
                805                 810                 815

Asp Lys Asp Val Arg Val Ala Phe Ser Gly Asn Ile Lys His Ile Leu
                820                 825                 830

Glu Ser Leu Asp Ser Asp Gly Phe Ile Lys Glu Leu Phe Val Leu
                835                 840                 845

Arg Met Lys Glu Ala Tyr Thr His Ala Gln Ile Ser Arg Asn Asn Glu
850                 855                 860

Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu His Cys Leu
                885                 890                 895

Leu Ser Lys Ser Ala Ser Val Ser Gly Ala Ala Tyr Thr Glu Ile Arg
                900                 905                 910

Ala Leu Val Ala Ala Lys Ser Val Lys Leu Gln Ser Phe Phe Ser Gln
                915                 920                 925

Tyr Lys Lys Pro Ile Cys Gln Phe Leu Val Glu Ser Leu His Ser Ser
                930                 935                 940

Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
                965                 970                 975

Glu Ile Ala Asn Val Phe Asp Phe Pro Asp Leu Asn Arg Phe Leu Thr
                980                 985                 990

Arg Thr Leu Gln Val Leu Leu Pro  Asp Leu Ala Ala Lys  Ala Ser Pro
                995                 1000                1005

Ala Ala  Ser Ala Leu Ile Arg  Thr Leu Gly Lys Gln  Leu Asn Val
        1010                1015                1020

Asn Arg  Arg Glu Ile Leu Ile  Asn Asn Phe Lys Tyr  Ile Phe Ser
        1025                1030                1035

His Leu  Val Cys Ser Cys Ser  Lys Asp Glu Leu Glu  Arg Ala Leu
        1040                1045                1050

His Tyr  Leu Lys Asn Glu Thr  Glu Ile Glu Leu Gly  Ser Leu Leu
        1055                1060                1065
```

```
Arg Gln Asp Phe Gln Gly Leu His Asn Glu Leu Leu Leu Arg Ile
    1070            1075                1080

Gly Glu His Tyr Gln Gln Val Phe Asn Gly Leu Ser Ile Leu Ala
    1085            1090                1095

Ser Phe Ala Ser Ser Asp Pro Tyr Gln Gly Pro Arg Asp Ile
    1100            1105                1110

Ile Ser Pro Glu Leu Met Ala Asp Tyr Leu Gln Pro Lys Leu Leu
    1115            1120                1125

Gly Ile Leu Ala Phe Phe Asn Met Gln Leu Leu Ser Ser Ser Val
    1130            1135                1140

Gly Ile Glu Asp Lys Lys Met Ala Leu Asn Ser Leu Met Ser Leu
    1145            1150                1155

Met Lys Leu Met Gly Pro Lys His Val Ser Ser Val Arg Val Lys
    1160            1165                1170

Met Met Thr Thr Leu Arg Thr Gly Leu Arg Phe Lys Asp Asp Phe
    1175            1180                1185

Pro Glu Leu Cys Cys Arg Ala Trp Asp Cys Phe Val Arg Cys Leu
    1190            1195                1200

Asp His Ala Cys Leu Gly Ser Leu Leu Ser His Val Ile Val Ala
    1205            1210                1215

Leu Leu Pro Leu Ile His Ile Gln Pro Lys Glu Thr Ala Ala Ile
    1220            1225                1230

Phe His Tyr Leu Ile Ile Glu Asn Arg Asp Ala Val Gln Asp Phe
    1235            1240                1245

Leu His Glu Ile Tyr Phe Leu Pro Asp His Pro Glu Leu Lys Lys
    1250            1255                1260

Ile Lys Ala Val Leu Gln Glu Tyr Arg Lys Glu Thr Ser Glu Ser
    1265            1270                1275

Thr Asp Leu Gln Thr Thr Leu Gln Leu Ser Met Lys Ala Ile Gln
    1280            1285                1290

His Glu Asn Val Asp Val Arg Ile His Ala Leu Thr Ser Leu Lys
    1295            1300                1305

Glu Thr Leu Tyr Lys Asn Gln Glu Lys Leu Ile Lys Tyr Ala Thr
    1310            1315                1320

Asp Ser Glu Thr Val Glu Pro Ile Ile Ser Gln Leu Val Thr Val
    1325            1330                1335

Leu Leu Lys Gly Cys Gln Asp Ala Asn Ser Gln Ala Arg Leu Leu
    1340            1345                1350

Cys Gly Glu Cys Leu Gly Glu Leu Gly Ala Ile Asp Pro Gly Arg
    1355            1360                1365

Leu Asp Phe Ser Thr Thr Glu Thr Gln Gly Lys Asp Phe Thr Phe
    1370            1375                1380

Val Thr Gly Val Glu Asp Ser Ser Phe Ala Tyr Gly Leu Leu Met
    1385            1390                1395

Glu Leu Thr Arg Ala Tyr Leu Ala Tyr Ala Asp Asn Ser Arg Ala
    1400            1405                1410

Gln Asp Ser Ala Ala Tyr Ala Ile Gln Glu Leu Leu Ser Ile Tyr
    1415            1420                1425

Asp Cys Arg Glu Met Glu Thr Asn Gly Pro Gly His Gln Leu Trp
    1430            1435                1440

Arg Arg Phe Pro Glu His Val Arg Glu Ile Leu Glu Pro His Leu
    1445            1450                1455

Asn Thr Arg Tyr Lys Ser Ser Gln Lys Ser Thr Asp Trp Ser Gly
```

-continued

```
            1460                1465                1470

Val Lys Lys Pro Ile Tyr Leu Ser Lys Leu Gly Ser Asn Phe Ala
    1475                1480                1485

Glu Trp Ser Ala Ser Trp Ala Gly Tyr Leu Ile Thr Lys Val Arg
    1490                1495                1500

His Asp Leu Ala Ser Lys Ile Phe Thr Cys Cys Ser Ile Met Met
    1505                1510                1515

Lys His Asp Phe Lys Val Thr Ile Tyr Leu Leu Pro His Ile Leu
    1520                1525                1530

Val Tyr Val Leu Leu Gly Cys Asn Gln Glu Asp Gln Gln Glu Val
    1535                1540                1545

Tyr Ala Glu Ile Met Ala Val Leu Lys His Asp Gln His Thr
    1550                1555                1560

Ile Asn Thr Gln Asp Ile Ala Ser Asp Leu Cys Gln Leu Ser Thr
    1565                1570                1575

Gln Thr Val Phe Ser Met Leu Asp His Leu Thr Gln Trp Ala Arg
    1580                1585                1590

His Lys Phe Gln Ala Leu Lys Ala Glu Lys Cys Pro His Ser Lys
    1595                1600                1605

Ser Asn Arg Asn Lys Val Asp Ser Met Val Ser Thr Val Asp Tyr
    1610                1615                1620

Glu Asp Tyr Gln Ser Val Thr Arg Phe Leu Asp Leu Ile Pro Gln
    1625                1630                1635

Asp Thr Leu Ala Val Ala Ser Phe Arg Ser Lys Ala Tyr Thr Arg
    1640                1645                1650

Ala Val Met His Phe Glu Ser Phe Ile Thr Glu Lys Lys Gln Asn
    1655                1660                1665

Ile Gln Glu His Leu Gly Phe Leu Gln Lys Leu Tyr Ala Ala Met
    1670                1675                1680

His Glu Pro Asp Gly Val Ala Gly Val Ser Ala Ile Arg Lys Ala
    1685                1690                1695

Glu Pro Ser Leu Lys Glu Gln Ile Leu Glu His Glu Ser Leu Gly
    1700                1705                1710

Leu Leu Arg Asp Ala Thr Ala Cys Tyr Asp Arg Ala Ile Gln Leu
    1715                1720                1725

Glu Pro Asp Gln Ile Ile His Tyr His Gly Val Val Lys Ser Met
    1730                1735                1740

Leu Gly Leu Gly Gln Leu Ser Thr Val Ile Thr Gln Val Asn Gly
    1745                1750                1755

Val His Ala Asn Arg Ser Glu Trp Thr Asp Glu Leu Asn Thr Tyr
    1760                1765                1770

Arg Val Glu Ala Ala Trp Lys Leu Ser Gln Trp Asp Leu Val Glu
    1775                1780                1785

Asn Tyr Leu Ala Ala Asp Gly Lys Ser Thr Thr Trp Ser Val Arg
    1790                1795                1800

Leu Gly Gln Leu Leu Leu Ser Ala Lys Lys Arg Asp Ile Thr Ala
    1805                1810                1815

Phe Tyr Asp Ser Leu Lys Leu Val Arg Ala Glu Gln Ile Val Pro
    1820                1825                1830

Leu Ser Ala Ala Ser Phe Glu Arg Gly Ser Tyr Gln Arg Gly Tyr
    1835                1840                1845

Glu Tyr Ile Val Arg Leu His Met Leu Cys Glu Leu Glu His Ser
    1850                1855                1860
```

-continued

```
Ile Lys Pro Leu Phe Gln His Ser Pro Gly Asp Ser Ser Gln Glu
1865                 1870                1875

Asp Ser Leu Asn Trp Val Ala Arg Leu Glu Met Thr Gln Asn Ser
1880                 1885                1890

Tyr Arg Ala Lys Glu Pro Ile Leu Ala Leu Arg Arg Ala Leu Leu
1895                 1900                1905

Ser Leu Asn Lys Arg Pro Asp Tyr Asn Glu Met Val Gly Glu Cys
1910                 1915                1920

Trp Leu Gln Ser Ala Arg Val Ala Arg Lys Ala Gly His His Gln
1925                 1930                1935

Thr Ala Tyr Asn Ala Leu Leu Asn Ala Gly Glu Ser Arg Leu Ala
1940                 1945                1950

Glu Leu Tyr Val Glu Arg Ala Lys Trp Leu Trp Ser Lys Gly Asp
1955                 1960                1965

Val His Gln Ala Leu Ile Val Leu Gln Lys Gly Val Glu Leu Cys
1970                 1975                1980

Phe Pro Glu Asn Glu Thr Pro Pro Glu Gly Lys Asn Met Leu Ile
1985                 1990                1995

His Gly Arg Ala Met Leu Leu Val Gly Arg Phe Met Glu Glu Thr
2000                 2005                2010

Ala Asn Phe Glu Ser Asn Ala Ile Met Lys Lys Tyr Lys Asp Val
2015                 2020                2025

Thr Ala Cys Leu Pro Glu Trp Glu Asp Gly His Phe Tyr Leu Ala
2030                 2035                2040

Lys Tyr Tyr Asp Lys Leu Met Pro Met Val Thr Asp Asn Lys Met
2045                 2050                2055

Glu Lys Gln Gly Asp Leu Ile Arg Tyr Ile Val Leu His Phe Gly
2060                 2065                2070

Arg Ser Leu Gln Tyr Gly Asn Gln Phe Ile Tyr Gln Ser Met Pro
2075                 2080                2085

Arg Met Leu Thr Leu Trp Leu Asp Tyr Gly Thr Lys Ala Tyr Glu
2090                 2095                2100

Trp Glu Lys Ala Gly Arg Ser Asp Arg Val Gln Met Arg Asn Asp
2105                 2110                2115

Leu Gly Lys Ile Asn Lys Val Ile Thr Glu His Thr Asn Tyr Leu
2120                 2125                2130

Ala Pro Tyr Gln Phe Leu Thr Ala Phe Ser Gln Leu Ile Ser Arg
2135                 2140                2145

Ile Cys His Ser His Asp Glu Val Phe Val Val Leu Met Glu Ile
2150                 2155                2160

Ile Ala Lys Val Phe Leu Ala Tyr Pro Gln Gln Ala Met Trp Met
2165                 2170                2175

Met Thr Ala Val Ser Lys Ser Ser Tyr Pro Met Arg Val Asn Arg
2180                 2185                2190

Cys Lys Glu Ile Leu Asn Lys Ala Ile His Met Lys Lys Ser Leu
2195                 2200                2205

Glu Lys Phe Val Gly Asp Ala Thr Arg Leu Thr Asp Lys Leu Leu
2210                 2215                2220

Glu Leu Cys Asn Lys Pro Val Asp Gly Ser Ser Ser Thr Leu Ser
2225                 2230                2235

Met Ser Thr His Phe Lys Met Leu Lys Lys Leu Val Glu Glu Ala
2240                 2245                2250

Thr Phe Ser Glu Ile Leu Ile Pro Leu Gln Ser Val Met Ile Pro
2255                 2260                2265
```

```
Thr Leu Pro Ser Ile Leu Gly Thr His Ala Asn His Ala Ser His
    2270            2275                2280
Glu Pro Phe Pro Gly His Trp Ala Tyr Ile Ala Gly Phe Asp Asp
    2285            2290                2295
Met Val Glu Ile Leu Ala Ser Leu Gln Lys Pro Lys Lys Ile Ser
    2300            2305                2310
Leu Lys Gly Ser Asp Gly Lys Phe Tyr Ile Met Met Cys Lys Pro
    2315            2320                2325
Lys Asp Asp Leu Arg Lys Asp Cys Arg Leu Met Glu Phe Asn Ser
    2330            2335                2340
Leu Ile Asn Lys Cys Leu Arg Lys Asp Ala Glu Ser Arg Arg Arg
    2345            2350                2355
Glu Leu His Ile Arg Thr Tyr Ala Val Ile Pro Leu Asn Asp Glu
    2360            2365                2370
Cys Gly Ile Ile Glu Trp Val Asn Asn Thr Ala Gly Leu Arg Pro
    2375            2380                2385
Ile Leu Thr Lys Leu Tyr Lys Glu Lys Gly Val Tyr Met Thr Gly
    2390            2395                2400
Lys Glu Leu Arg Gln Cys Met Leu Pro Lys Ser Ala Ala Leu Ser
    2405            2410                2415
Glu Lys Leu Lys Val Phe Arg Glu Phe Leu Leu Pro Arg His Pro
    2420            2425                2430
Pro Ile Phe His Glu Trp Phe Leu Arg Thr Phe Pro Asp Pro Thr
    2435            2440                2445
Ser Trp Tyr Ser Ser Arg Ser Ala Tyr Cys Arg Ser Thr Ala Val
    2450            2455                2460
Met Ser Met Val Gly Tyr Ile Leu Gly Leu Gly Asp Arg His Gly
    2465            2470                2475
Glu Asn Ile Leu Phe Asp Ser Leu Thr Gly Glu Cys Val His Val
    2480            2485                2490
Asp Phe Asn Cys Leu Phe Asn Lys Gly Glu Thr Phe Glu Val Pro
    2495            2500                2505
Glu Ile Val Pro Phe Arg Leu Thr His Asn Met Val Asn Gly Met
    2510            2515                2520
Gly Pro Met Gly Thr Glu Gly Leu Phe Arg Arg Ala Cys Glu Val
    2525            2530                2535
Thr Met Arg Leu Met Arg Asp Gln Arg Glu Pro Leu Met Ser Val
    2540            2545                2550
Leu Lys Thr Phe Leu His Asp Pro Leu Val Glu Trp Ser Lys Pro
    2555            2560                2565
Val Lys Gly His Ser Lys Ala Pro Leu Asn Glu Thr Gly Glu Val
    2570            2575                2580
Val Asn Glu Lys Ala Lys Thr His Val Leu Asp Ile Glu Gln Arg
    2585            2590                2595
Leu Gln Gly Val Ile Lys Thr Arg Asn Arg Val Thr Gly Leu Pro
    2600            2605                2610
Leu Ser Ile Glu Gly His Val His Tyr Leu Ile Gln Glu Ala Thr
    2615            2620                2625
Asp Glu Asn Leu Leu Cys Gln Met Tyr Leu Gly Trp Thr Pro Tyr
    2630            2635                2640
Met

<210> SEQ ID NO 3
```

-continued

```
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  Serine at position 8 is
      phosphorylated

<400> SEQUENCE: 3

Ser Ser Asn Ser Asp Gly Ile Ser Pro Lys Arg Arg Arg Leu Ser
1               5                   10                  15

<210> SEQ ID NO 4
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  Serine at position 8 is
      phosphorylated

<400> SEQUENCE: 4

Lys Lys Ile Ser Leu Lys Gly Ser Asp Gly Lys Phe Tyr Ile Met
1               5                   10                  15

<210> SEQ ID NO 5
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION:  Serine at position 7 is
      phosphorylated

<400> SEQUENCE: 5

Ser Asn Ser Asp Gly Ile Ser Pro Lys Arg Arg Arg Leu
1               5                   10

<210> SEQ ID NO 6
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION:  Serine at position 6 is
      phosphorylated

<400> SEQUENCE: 6

Ile Ser Leu Lys Gly Ser Asp Gly Lys Phe Tyr
1               5                   10

<210> SEQ ID NO 7
<211> LENGTH: 30
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION:  Serine at position 10 is
      phosphorylated

<400> SEQUENCE: 7

Asn Leu Ser Ser Asn Ser Asp Gly Ile Ser Pro Lys Arg Arg Arg Leu
1               5                   10                  15

Ser Ser Ser Leu Asn Pro Ser Lys Arg Ala Pro Lys Gln Thr
                20                  25                  30
```

```
<210> SEQ ID NO 8
<211> LENGTH: 32
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION:  Serine at position 20 is
      phosphorylated

<400> SEQUENCE: 8

Asp Met Val Glu Ile Leu Ala Ser Leu Gln Lys Pro Lys Lys Ile Ser
1               5                   10                  15

Leu Lys Gly Ser Asp Gly Lys Phe Tyr Ile Met Met Cys Lys Pro Lys
            20                  25                  30
```

US 7,906,297 B2

REAGENTS FOR THE DETECTION OF PHOSPHORYLATED ATR KINASE (SER 428) AND USES THEREOF

RELATED APPLICATIONS

This application claims priority to, and the benefit of, U.S. Ser. No. 60/700,979, filed Jul. 20, 2005, the disclosure of which is hereby incorporated by reference.

FIELD OF THE INVENTION

The invention relates generally to antibodies and peptide reagents for the detection of protein phosphorylation, and to protein phosphorylation in cancer.

BACKGROUND OF THE INVENTION

The activation of proteins by post-translational modification is an important cellular mechanism for regulating most aspects of biological organization and control, including growth, development, homeostasis, and cellular communication. Protein phosphorylation, for example, plays a critical role in the etiology of many pathological conditions and diseases, including cancer, developmental disorders, autoimmune diseases, and diabetes. Yet, in spite of the importance of protein modification, it is not yet well understood at the molecular level, due to the extraordinary complexity of signaling pathways, and the slow development of technology necessary to unravel it.

Protein phosphorylation on a proteome-wide scale is extremely complex as a result of three factors: the large number of modifying proteins, e.g. kinases, encoded in the genome, the much larger number of sites on substrate proteins that are modified by these enzymes, and the dynamic nature of protein expression during growth, development, disease states, and aging. The human genome, for example, encodes over 520 different protein kinases, making them the most abundant class of enzymes known. See Hunter, Nature 411: 355-65 (2001). Most kinases phosphorylate many different substrate proteins, at distinct tyrosine, serine, and/or threonine residues. Indeed, it is estimated that one-third of all proteins encoded by the human genome are phosphorylated, and many are phosphorylated at multiple sites by different kinases.

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Understanding which proteins are modified by these kinases will greatly expand our understanding of the molecular mechanisms underlying oncogenic transformation. Therefore, the identification of, and ability to detect, phosphorylation sites on a wide variety of cellular proteins is crucially important to understanding the key signaling proteins and pathways implicated in the progression of diseases like cancer.

Deregulation of kinases is a central theme in the etiology of cancers. Constitutively active kinases can contribute not only to unrestricted cell proliferation, but also to other important features of malignant tumors, such as evading apoptosis, the ability to promote blood vessel growth, the ability to invade other tissues and build metastases at distant sites (see e.g. Blume-Jensen et al., Nature 411: 355-365 (2001)). These effects are mediated not only through aberrant activity of receptor kinase themselves, but, in turn, by aberrant activity of their downstream signaling molecules and substrates, including kinases.

Among such kinases is ataxia-telangiectasia and Rad3-related (ATR) kinase, a serine/threonine protein kinase that is implicated in cellular DNA damage repair processes and cell cycle signaling. Mutations of ATR have been linked to cancers of the stomach and endometrium, and lead to increased sensitivity to ionizing radiation and abolished cell cycle checkpoints. ATR is essential for the viability of somatic cells, and deletion of ATR has been shown to result in loss of damage checkpoint responses and cell death. See Cortez et al., Science 294: 1713-1716 (2001). ATR is also essential for the stability of fragile sites, and low ATR expression in Seckel syndrome patients results in increased chromosomal breakage following replication stress. See Casper et al., Am. J. Hum. Genet 75: 654-660 (2004). The replication protein A (RPA) complex recruits ATR, and its interacting protein ATRIP, to sites of DNA damage, and ATR itself mediates the activation of the CHK1 signaling cascade. See Zou et al., Science 300:1542-1548 (2003). ATR, like its related checkpoint kinase ATM, phosphorylates RAD17 early in a cascade that is critical to for checkpoint signaling in DNA-damaged cells. See Bao et al., Nature 411: 969-974 (2001). It is believed that ATR is particularly essential in the early mammalian embryo, to sense incomplete DNA replication and prevent mitotic catastrophe.

Despite the essential role of ATR in cell cycle signaling and DNA repair processes, little is known about its activation, and there are no known phosphorylation sites on this protein. Since kinase activity is regulated through phosphorylation, there remains a need for identifying phosphorylation sites on ATR, and for subsequently developing novel reagents to study the phosphorylation of ATR at such sites. Identifying particular phosphorylation sites on ATR and providing new reagents to detect and quantify them remains especially important to advancing our understanding of the regulation of ATR and the role it plays in cell cycling, DNA repair, and disease.

SUMMARY OF THE INVENTION

The invention discloses two novel human ATR kinase phosphorylation sites, serine 428 (Ser428) and serine 2317 (Ser2317), as well as homologous sites other mammals, and provides antibodies and AQUA peptides that selectively bind to and/or detect ATR when phosphorylated at these sites. Also provided are methods for determining the phosphorylation of ATR in a biological sample, profiling ATR activation in a test tissue, and identifying a compound that modulates expression and/or activity of ATR, by using a detectable reagent, such as the disclosed antibodies or AQUA peptides, that selectively binds to and or quantifies ATR when phosphorylated at Ser428 and/or Ser2317, respectively.

BRIEF DESCRIPTION OF THE DRAWINGS

FIG. 1—is the amino acid sequence (1-letter code) of human ATR kinase (SEQ ID NO: 1) (Swiss Prot Acc# Q13535). Ser428 and Ser2317 are underlined, and the peptide sequences encompassing Ser428 and Ser2317, respectively, and corresponding to the immunogen used to generate exemplary ATR(Ser428) and ATR(Ser2317) phosphospecific antibodies are indicated in bold (see Example 1).

FIG. 2—is the amino acid sequence (1-letter code) of mouse ATR (SEQ ID NO: 2) (SwissProt Acc# Q9JKK8). Ser419 and Ser2296 are underlined, and the peptide sequences encompassing Ser419 and Ser2296, respectively, corresponding to the highly homologous sequences of the human ATR (Ser428, Ser2317) phosphorylation sites are indicated in bold (see FIG. 1).

DETAILED DESCRIPTION OF THE INVENTION

Figure 3:
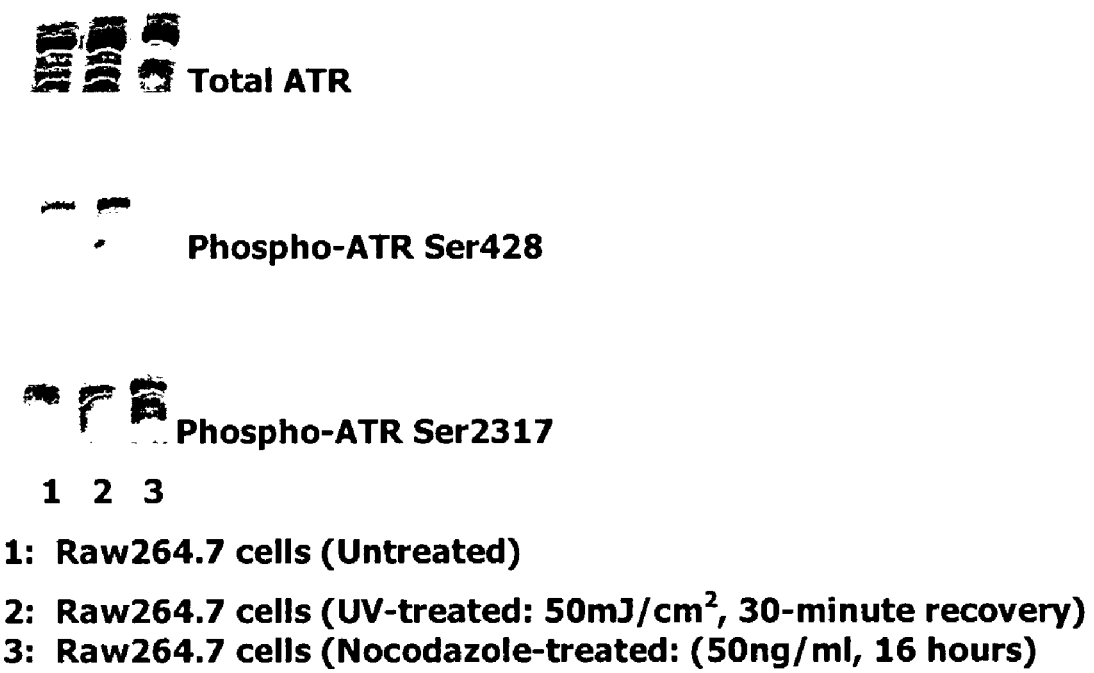
FIG. 3—shows Western blot analyses using phospho-ATR (Ser428) and phospho-ATR(Ser2317) polyclonal antibodies and 264.7 cells, treated with either Nocodazole or ultraviolet radiation (UV).

In accordance with the present invention, two novel sites of ATR kinase phosphorylation, serine 428 (Ser428) and serine 2317 (Ser2317) in the human sequence (see FIG. 1), have now been identified. Highly homologous novel phosphorylation sites in murine ATR, serine 419 (Ser419) and serine 2296 (Ser2296) (see FIG. 2), have also been identified. Although ATR kinase plays a critical role in DNA damage repair and cell cycle checkpoint signaling, the presently disclosed phosphorylation sites were previously been unknown.

The ATR Ser428 and Ser2317 phosphorylation sites were identified/predicted by analyzing the human ATR amino acid sequence with the ScanSite program (http://scansite.mit.edu) (see also Yaffe et al., *Nat Biotechnol.* 19(4): 348-53 (2001)). This algorithm searches for motifs within proteins that are likely to be phosphorylated by specific protein kinases or bind to domains such as SH2 domains, 14-3-3 domains or PDZ domains. Optimal phosphorylation sites for particular serine/threonine protein kinases or tyrosine protein kinases are predicted using a matrix of selectivity values for amino acids at each position relative to the phosphorylation site, as determined from the oriented peptide library technique described by Songyang et al., Current Biology 4: 973-982 (1994) and Songyang et al., Nature 373: 536-539 (1995).

Analysis of the human ATR kinase protein sequence with ScanSite with high stringency revealed five (5) potential Ser/Thr phosphorylation sites, including putative Cdc2, Cdk5, Casein Kinase 1 and PKC zeta, PKC mu and DNA-PK sites. Attention was focused on the Cdc2/Cdk5 and PKC zeta sites. The two sites identified, numbered according to human ATR (FIG. 1, SEQ ID NO: 1), all include a typical PKC consensus (KXX*SXXK) motif or a proline directed kinase motif sequence, and are (phosphorylated serine indicated by bold *S):

```
Ser428:    SSNSDGI*SPKRRRLS    (SEQ ID NO: 3)

Ser2317:   KKISLKG*SDGKFYIM    (SEQ ID NO: 4)
```

Phosphorylation of human ATR at Ser428 and Ser2317 was confirmed using exemplary phospho-specific antibodies of the invention (see Examples). As a result of this discovery, reagents may now be produced that only detect ATR kinase when phosphorylated at either of these sites. For example, peptide antigens may now be designed to raise phospho-specific antibodies that bind ATR only when phosphorylated at Ser428 or Ser2317 in the human ATR sequence, and/or to the equivalent and highly homologous sites in mouse ATR (Ser419, Ser2296), or other species, such as Xenopus laevis (Ser2328).

The discovery of novel ATR kinase phosphorylation sites described herein enables the production, by standard methods, of new reagents, such as phosphorylation site-specific antibodies and AQUA peptides (heavy-isotope labeled peptides), capable of specifically detecting and/or quantifying these phosphorylated sites/proteins. Such reagents are highly useful, inter alia, for studying signal transduction events underlying the progression of diseases, like cancer, involving aberrant DNA damage repair and cell cycle checkpoint signaling. Accordingly, the invention provides novel reagents—phospho-specific antibodies and AQUA peptides—for the specific detection and/or quantification of ATR kinase only when phosphorylated (or only when not phosphorylated) at a particular phosphorylation site disclosed herein. The invention also provides methods of detecting and/or quantifying phosphorylated ATR using the phosphorylation-site specific antibodies and AQUA peptides of the invention.

In part, the invention provides an isolated phosphorylation site-specific antibody that specifically binds human ATR kinase only when phosphorylated at serine 428 or serine 2317, respectively, and does not bind the unphosphorylated form of the protein and/or other phosphorylation sites on ATR. In further part, the invention provides a heavy-isotope labeled peptide (AQUA peptide) for the detection and quantification of human ATR kinase, the labeled peptide comprising a phosphorylation site sequence encompassing either serine 428 or serine 2317 in the human ATR sequence (see FIG. 1). Preferred AQUA peptides of the invention are tryptic digest fragments that encompass either of the novel phosphorylation sites disclosed herein, as further described below. Antibodies and AQUA peptides for detecting highly homologous phosphorylation sites in other species, such as mouse and Xenopus, as discussed above, are within the scope of the present invention.

Also provided are methods of using a detectable reagent that binds to phosphorylated ATR (Ser428 and Ser2317) to detect ATR phosphorylation and activation in a biological sample or test tissue potentially containing, or suspected of containing, phosphorylated ATR, or having altered ATR expression or activity, as further described below. In a preferred embodiment, the detectable reagent is at least one ATR (Ser428, Ser2317) antibody of the invention, and the sample or tissue is taken from a subject potentially having, or suspected of having, altered ATR activity. In another preferred embodiment, the detectable reagent is an AQUA peptide of the invention.

The further aspects, advantages, and embodiments of the invention are described in more detail below. All references cited herein are hereby incorporated by reference.

A. Antibodies and Cell Lines

ATR phospho-specific antibodies of the invention bind to human ATR only when phosphorylated at Ser428 or Ser2317, respectively, and do not substantially bind to ATR when not phosphorylated at either these respective residues, nor to ATR when phosphorylated at other phosphorylation sites. The ATR antibodies may also bind highly homologous and equivalent ATR sites in other species, for example mouse ATR (Ser419) and/or ATR (Ser2296), respectively, as disclosed herein.

ATR antibodies of the invention include (a) monoclonal antibodies that bind phospho-ATR (Ser428) or phospho-ATR (Ser2317), (b) polyclonal antibodies which bind to phospho-ATR (Ser428) and/or phospho-ATR (Ser2317), (c) antibodies (monoclonal or polyclonal) which specifically bind to the phospho-antigen (or more preferably the epitope) bound by the exemplary ATR (Ser428, Ser2317) antibodies disclosed in the Examples herein, (d) antibodies as described in (a)-(c) above that bind equivalent phosphorylation ATR and/or ATR sites in other species (e.g. mouse, rat), as disclosed herein, and (e) fragments of (a), (b), (c), or (d) above which bind to the antigen (or more preferably the epitope) bound by the exemplary antibodies disclosed herein. Such antibodies and antibody fragments may be produced by a variety of techniques well known in the art, as discussed below. Antibodies that bind to the phosphorylated epitope (i.e., the specific binding site) bound by the exemplary ATR (Ser428, Ser2317) antibodies of the Examples herein can be identified in accordance with known techniques, such as their ability to compete with labeled ATR antibodies in a competitive binding assay.

The preferred epitopic site of the human ATR (Ser428, Ser2317) antibodies of the invention is a peptide fragment consisting essentially of about 11 to 17 amino acids including the phosphorylated serine 428 or serine 2317, wherein about 5 to 8 amino acids are positioned on each side of the serine phosphorylation site (for example, residues 427-433 of SEQ ID NO: 1, or residues 2312-2322 of SEQ ID NO: 1). These epitopic sites, for example, correspond to the following equivalent murine sites: residues 414-424 of SEQ ID NO: 2 (mouse ATR) (encompassing Ser419) and residues 2291-2301 of SEQ ID NO: 2 (mouse ATR) encompassing Ser2296).

The invention is not limited to ATR antibodies, but includes equivalent molecules, such as protein binding domains or nucleic acid aptamers, which bind, in a phospho-specific manner, to essentially the same phosphorylated epitope to which the ATR antibodies of the invention bind. See, e.g., Neuberger et al., *Nature* 312: 604 (1984). Such equivalent non-antibody reagents may be suitably employed in the methods of the invention further described below.

The term "antibody" or "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.)

The term "ATR antibodies" is used interchangeably with the term "ATR (Ser428, Ser2317) antibodies" which means antibodies that specifically bind phospho-ATR (Ser428) or phospho-ATR (Ser2317) (in the human sequence), both monoclonal and polyclonal, as disclosed herein. The term includes antibodies that bind equivalent and highly-homologous sites in ATR from other species, for example, murine ATR (Ser419, Ser2296), Xenopus laevis ATR (Ser2328), etc. The term "does not bind" with respect to disclosed antibodies means does not substantially react with as compared to binding to phospho-ATR and/or phospho-ATR. The term includes antibodies that bind whole protein comprising the target phosphorylation site, as well as shorter ATR polypeptides or fragments comprising the phosphorylated serine residue (e.g. a polypeptide of 5-25 or 25-50 or more residues comprising the target phosphorylation site).

The term "detectable reagent" means a molecule, including an antibody, peptide fragment, binding protein domain, etc., the binding of which to a desired target is detectable or traceable. Suitable means of detection are described below.

Polyclonal antibodies of the invention may be produced according to standard techniques by immunizing a suitable animal (e.g., rabbit, goat, etc.) with an antigen encompassing phospho-Ser428 or phospho-Ser2317 (human ATR sequence), collecting immune serum from the animal, and separating the polyclonal antibodies from the immune serum, in accordance with known procedures. In a preferred embodiment, the antigen is a phospho-peptide antigen comprising the human ATR sequence surrounding and including phospho-Ser428 or phospho-Ser2317, respectively, the antigen being selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85:21-49 (1962)).

Particularly preferred peptide antigens, SNSDGI*SPKRRRL (SEQ ID NO: 5), and ISLKG*SDGKFY (SEQ ID NO: 6) (where *S=phosphoserine) (corresponding to the ATR Ser428 and Ser2317 phosphorylation sites, respectively (see FIG. 1) are described in Example 1, below. It will be appreciated by those of skill in the art that longer or shorter phosphopeptide antigens may be employed. See Id. Polyclonal ATR antibodies produced as described herein may be screened as further described below. These preferred antigens corresponds to the equivalent phosphorylation sites in murine ATR (see FIG. 2).

Monoclonal antibodies of the invention may be produced in a hybridoma cell line according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)).

The invention also provides hybridoma clones, constructed as described above, that produce ATR monoclonal antibodies of the invention. Similarly, the invention includes recombinant cells producing a phospho-ATR (Ser428, Ser2317) antibody as disclosed herein, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

ATR antibodies of the invention, whether polyclonal or monoclonal, may be screened for epitope and phospho-specificity according to standard techniques. See, e.g. *Czernik et al., Methods in Enzymology,* 201: 264-283 (1991). For example, the antibodies may be screened against the phospho and non-phospho peptide library by ELISA to ensure specificity for both the desired antigen (i.e. that epitope including Ser428, Ser2317) and for reactivity only with the phosphorylated form of the antigen. Peptide competition assays may be carried out to confirm lack of reactivity with other ATR phospho-epitopes. The antibodies may also be tested by Western blotting against cell preparations containing ATR, e.g. cell lines over-expressing ATR, to confirm reactivity with the desired phosphorylated target. Specificity against the desired phosphorylated epitopes may also be examined by construction ATR mutants lacking phosphorylatable residues at positions outside the desired epitope known to be phosphorylated, or by mutating the desired phospho-epitope and confirming lack of reactivity. ATR antibodies of the invention may exhibit some limited cross-reactivity with non-ATR epitopes. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-ATR proteins is readily characterized by Western blotting alongside markers of known molecular weight. Amino acid sequences of cross-reacting proteins may be examined to identify sites highly homologous to the human ATR sequence surrounding Ser428, Ser2317.

ATR antibodies may be further characterized via immunohistochemical (IHC) staining using normal and diseased tissues to examine ATR phosphorylation and activation status in diseased tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

ATR antibodies of the invention bind to human ATR when phosphorylated at the Ser428 or Ser2317 site, respectively, but are not limited only to the human species, per se. Phospho-specific antibodies that bind conserved and highly homologous phosphorylation sites in other species (e.g. mouse, rat, monkey, *Xenopus*, yeast), in addition to binding the human ATR (pSer428, pSer2317) sites, are within the scope of the present invention. For example, ATR antibodies provided may also bind the highly homologous Ser419 and/or Ser2296 sites in mouse ATR, respectively, as well as the homologous Ser2328 site in *Xenopus laevis* ATR (Swiss Prot acc. no. Q13535). Additional highly homologous sites conserved in other species, which are in within the scope of the invention, can readily be identified by standard sequence comparisons, such as using BLAST, with the human ATR and mouse ATR sites disclosed herein.

C. Heavy-Isotope Labeled Peptides (AQUA Peptides).

The novel ATR kinase phosphorylation sites disclosed herein now enable the production of corresponding heavy-isotope labeled peptides for the absolute quantification of such signaling proteins (both phosphorylated and not phosphorylated at a disclosed site) in biological samples. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}$C, $^{15}$N). The result is a peptide that is chemically identical to its native counterpart formed by proteolysis, but is easily distinguishable by MS via a 7-Da mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP- LC-MS/MS method within a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragment masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

In accordance with the present invention, AQUA internal peptide standards (heavy-isotope labeled peptides) may now be produced, as described above, for either of the novel human ATR kinase protein phosphorylation sites disclosed herein. Peptide standards for a phosphorylation site (e.g. the serine 428 site in human ATR (see FIG. 1)) may be produced for both the phosphorylated and non-phosphorylated forms of the site, and such standards employed in the AQUA methodology to detect and quantify both forms of such ATR phosphorylation site in a biological sample.

AQUA peptides of the invention may comprise an ATR peptide sequence, typically eight to forty amino acids in length, which encompasses the phosphorylatable serine (Ser428 or Ser2317) of interest (see FIG. 1). For example, an AQUA peptide of the invention for detection/quantification of human ATR kinase when phosphorylated at serine 428 may consist of, or comprise, the sequence DGIs*PKRRRL (s*=phosphoserine), which comprises phosphorylatable serine 428 (see FIG. 1) (SEQ ID NO: 1)). Longer peptides corresponding to particular digestion fragments may be desirable, and exemplary fragments are described in Example 4 below. Heavy-isotope labeled equivalents of a particular ATR peptide (encompassing either the Ser428 or Ser2317 sites disclosed herein) can be readily synthesized, both in phosphorylated and unphosphorylated form, and their unique MS and LC-SRM signature determined, so that the peptides are validated as AQUA peptides and ready for use in quantification experiments. AQUA peptides for quantifying or detecting highly homologous ATR phospho-sites in other species (e.g. mouse, as disclosed herein) may similarly be constructed.

Particularly preferred ATR peptides suitable for development of corresponding AQUA peptides are those peptides (encompassing either serine 428 or serine 2317) that are produced by enzymatic digestion (e.g. with trypsin, GluC, AspN, etc.) of ATR (SEQ ID NO: 1). Heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments. Such digestion fragments may be shorter or larger ATR peptides, and the selection and production of preferred AQUA peptides may be carried out as described above (see Gygi et al., Gerber et al. supra.). Two exemplary digestion fragments are described in Example 4 below.

AQUA peptides of the invention may also be employed within a kit that comprises one or multiple AQUA peptide(s) provided, and, optionally, a second detecting reagent conjugated to a detectable group. For example, a kit may include AQUA peptides for both the phosphorylated and non-phosphorylated form of a phosphorylation site disclosed herein. The reagents may also include ancillary agents such as buffering agents and protein stabilizing agents, e.g., polysaccharides and the like. The kit may further include, where necessary, enzyme substrates, agents for reducing background interference in a test, control reagents, apparatus for conducting a test, and the like. The test kit may be packaged in any suitable manner, typically with all elements in a single container along with a sheet of printed instructions for carrying out the test.

AQUA peptides provided by the invention will be highly useful, among other things, in the further study of ATR kinase signaling, aberrations in ATR activity underlying disease, and/or in monitoring the effects of test compounds on ATR and ATR-mediated signal transduction proteins and pathways.

D. Detection & Profiling Methods

The methods disclosed herein may be employed with any biological sample potentially containing, or suspected of containing, phosphorylated ATR kinase. Biological samples taken from a mammal, e.g. a human a subject, for use in the methods disclosed herein are generally biological fluids such as serum, blood plasma, fine needle aspirant, ductal lavage; bone marrow sample or ascites fluid. In the alternative, the sample taken from the subject can be a tissue sample (e.g., a biopsy tissue), such as bone marrow or tumor tissue, or a cell lysate, whether or not purified.

In one embodiment, the invention provides a method for detecting phosphorylated ATR in a biological sample by (a) contacting a biological sample potentially (or suspected of) containing phosphorylated ATR and/or phosphorylated ATR with at least one detectable reagent that binds to and/or detects human ATR only when phosphorylated at Ser428 or Ser2317, respectively, under conditions suitable for formation of a reagent-ATR complex, and (b) detecting the presence of the complex in the sample, wherein the presence of the complex indicates the presence of phosphorylated ATR (Ser428) and/or phosphorylated ATR (Ser2317) in the sample.

In a preferred embodiment, the reagent is an ATR phospho-specific antibody of the invention. In another preferred embodiment, the reagent is an ATR heavy isotope-labeled peptide (AQUA peptide of the invention. In other preferred embodiments, the biological sample has been contacted with at least one modulator of ATR activity, e.g. an ATR inhibitor, or is obtained from a subject treated with such modulator. Changes in ATR(Ser428 and/or Ser2317) phosphorylation resulting from contacting a biological sample with a test compound, such as an AKT inhibitor, may be examined to determine the effect of such compound. The compound may be a "pan" kinase inhibitor that inhibits more than type of kinase including ATR (for example, bis-indoleimide), or may be a specific inhibitor of ATR kinase. The inhibitor may inhibit the expression and/or activity of ATR. Exemplary inhibitors of ATR include, but are not limited to, caffeine.

Inhibitory compounds may be targeted inhibitors that modulate post-translational activity of ATR, or may be upstream expression inhibitors, such as siRNA or anti-sense inhibitors. In another preferred embodiment, the compound is being tested for inhibition of ATR activity or expression. Such compound may, for example, directly inhibit ATR activity, or may indirectly inhibit its activity by, e.g., inhibiting another kinase that phosphorylates and thus activates ATR, or by inhibiting co-factors or necessary binding partners or complex partners of ATR. Likewise, modulators that enhance the activity and/or expression of ATR may be similarly targeted or general modulators, or direct or indirect modulators, as described above.

Biological samples may be obtained from subjects at risk of, potentially, or suspected of, having a disease or condition involving altered ATR expression or activity (e.g., Seckel syndrome). For example, samples may be analyzed to monitor subjects who have been previously diagnosed as having Seckel syndrome, to screen subjects who have not been previously diagnosed as having this disease, or to monitor the desirability or efficacy of therapeutics targeted at modulating the activity of ATR.

In another embodiment, the invention provides a method for profiling ATR phosphorylation in a test tissue potentially having (or suspected of involving) altered ATR expression and/or activity, by (a) contacting the test tissue with at least one detectable reagent that binds to and/or detects human ATR only when phosphorylated at Ser428 or Ser2317, respectively, under conditions suitable for formation of a reagent-ATR complex, (b) detecting the presence of the complex in the test tissue, wherein the presence of the complex indicates the presence of phosphorylated ATR (Ser428) or phosphorylated ATR (Ser2317) in the test tissue, and (c) comparing the presence of phosphorylated ATR detected in step (b) with the presence of phosphorylated ATR (Ser428, Ser2317) in a control tissue, wherein a difference in ATR phosphorylation profiles between the test and control tissues indicates altered ATR expression and/or activation in the test tissue. In a preferred embodiment, the reagent is an ATR phospho-specific antibody of the invention. In another preferred embodiment, the reagent is an ATR AQUA peptide of the invention.

The methods described above are applicable to examining tissues or samples from any disease or condition involving or characterized by altered ATR expression and/or activity, in which phosphorylation of ATR at Ser428 and/or Ser2317, respectively, (and possibly other serine residues) has predictive value as to the outcome of the disease or the response of the disease to therapy. It is anticipated that the ATR antibodies and AQUA peptides will have diagnostic utility in a disease characterized by, or involving, altered ATR phosphorylation and/or signaling. The methods are applicable, for example, where samples are taken from a subject has not been previously diagnosed as having a disease characterized by altered ATR expression and/or activity, nor has yet undergone treatment for the disease, and the method is employed to help diagnose the disease, or monitor the possible progression of the condition, or assess risk of the subject developing disease involving altered ATR (Ser428, Ser2317) phosphorylation.

Such diagnostic assay may be carried out prior to preliminary blood, fluid, or tissue evaluation or surgical surveillance procedures. Such a diagnostic assay may be employed to identify patients with activated or inhibited ATR, who would be most likely to respond to therapeutics targeted at activating or inhibiting ATR activity. Such a selection of patients would be useful in the clinical evaluation of efficacy of future ATR—targeted therapeutics as well as in the future prescription of such drugs to patients. Alternatively, the methods are applicable where a subject has been previously diagnosed as having a disease involving altered ATR signaling, such as Seckel syndrome, and possibly has already undergone treatment for the disease, and the method is employed to monitor the progression of the disease, or the treatment thereof.

In another embodiment, the invention provides a method for identifying a compound which modulates phosphorylation of ATR in a test tissue, by (a) contacting the test tissue with the compound, (b) detecting the level of phosphorylated ATR and/or ATR in said the test tissue of step (a) using at least one detectable reagent that binds to and/or detects ATR when phosphorylated at Ser428 or Ser2317 under conditions suitable for formation of a reagent-ATR complex, and (c) comparing the level of phosphorylated ATR and/or ATR detected in step (b) with the presence of phosphorylated ATR (Ser428, Ser2317) in a control tissue not contacted with the compound, wherein a difference in ATR phosphorylation levels between the test and control tissues identifies the compound as a modulator of ATR phosphorylation. In a preferred embodiment, the reagent is an ATR antibody or an AQUA peptide of the invention. The compound may modulate ATR activity either positively or negatively, for example by increasing or decreasing phosphorylation or expression of ATR. Alternatively, ATR phosphorylation may be monitored to determine the efficacy of a compound targeted at any kinase that phosphorylates ATR (Ser428) and/or ATR (Ser2317), or any phosphatase that de-phosphorylates ATR at one or both of these sites.

Conditions suitable for the formation of antibody-antigen complexes or reagent-ATR complexes are well known in the art (see part (d) below and references cited therein). It will be understood that more than one ATR phospho-specific antibody may be used in the practice of the above-described methods. For example, a phospho-ATR (Ser428, Ser2317) antibody and a phospho-specific antibody to another serine, tyrosine, or threonine phosphorylation site may be simultaneously employed to detect phosphorylation of both sites in one step.

E. Immunoassay Formats & Diagnostic Kits

Assays carried out in accordance with methods of the present invention may be homogeneous assays or heterogeneous assays. In a homogeneous assay the immunological reaction usually involves an ATR-specific reagent (e.g. a ATR phospho-antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immuno-chemical labels that may be employed include free radicals, radio-isotopes, fluorescent dyes, enzymes, bacteriophages, coenzymes, and so forth.

In a heterogeneous assay approach, the reagents are usually the specimen, an ATR-specific reagent (e.g., the ATR antibody of the invention), and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of phosphorylated ATR is detectable compared to background.

ATR antibodies disclosed herein may be conjugated to a solid support suitable for a diagnostic assay (e.g., beads, plates, slides or wells formed from materials such as latex or polystyrene) in accordance with known techniques, such as precipitation. Antibodies of the invention, or other ATR binding reagents, may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

ATR phospho-specific antibodies of the invention may also be used in a flow cytometry assay to determine the activation status of ATR in patients before, during, and after treatment with a drug targeted at inhibiting ATR phosphorylation at Ser428 and/or Ser2317. For example, bone marrow cells or peripheral blood cells from patients may be analyzed by flow cytometry for ATR phosphorylation, as well as for markers identifying various hematopoietic cell types. In this manner, ATR activation status of the diseased cells may be specifically characterized.

Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 2% paraformaldehyde for 20 minutes at 37° C. followed by permeabilization in 90% methanol for 30 minutes on ice. Cells may then be stained with the primary ATR antibody, washed and labeled with a fluorescent-labeled secondary antibody. The cells would then be analyzed on a flow cytometer (e.g. a Beckman Coulter EPICS-XL) according to the specific protocols of the instrument used. Such an analysis would identify the presence of phosphorylated ATR (Ser428, Ser2317) in a cell of interest and reveal the drug response on the targeted kinase.

Diagnostic kits for carrying out the methods disclosed above are also provided by the invention. Such kits comprise at least one detectable reagent that binds to or detects human ATR only when phosphorylated at Ser428 or Ser2317, respectively. In a preferred embodiment, the reagent is an ATR phospho-specific antibody of the invention. In another preferred embodiment, the reagent is an ATR AQUA peptide of the invention. In one embodiment, the invention provides a kit for the detection of phosphorylated ATR (Ser428) and/or ATR (Ser2317) in a biological sample comprising at least one ATR specific reagent of the invention (i.e. a phospho-specific antibody that binds phospho-ATR (Ser428, Ser2317)). The kit may also include one or more secondary reagents, such as a secondary antibody, or ancillary agents such as buffering agents and protein stabilizing agents, e.g., polysaccharides and the like. The diagnostic kit may further include, where necessary, other enzyme substrates, agents for reducing background interference in a test, control reagents, apparatus for conducting a test, and the like.

The following Examples are provided only to further illustrate the invention, and are not intended to limit its scope, except as provided in the claims appended hereto. The present invention encompasses modifications and variations of the methods taught herein which would be obvious to one of ordinary skill in the art.

Example 1

Production of a Human ATR (Ser428) Phospho-Specific Antibody

A previously unknown ATR phosphorylation site, serine 428, was identified as described above by predictive analysis of the human ATR protein sequence using the ScanSite program. Yaffe et al., supra. A 13 amino acid phospho-peptide antigen, SNSDGI*SPKRRRL (SEQ ID NO: 5) (where *S=phosphoserine), corresponding to residues 422-434 of human ATR (see SEQ ID NO: 1; FIG. 1), was constructed according to standard synthesis techniques using a Rainin/Protein Technologies, Inc., Symphony peptide synthesizer. See ANTIBODIES: A LABORATORY MANUAL, supra.; Merrifield, supra. This peptide antigen also corresponds to a highly homologous site in murine ATR (see FIG. 2; SEQ ID NO: 2).

This peptide was coupled to KLH, and rabbits were injected intradermally (ID) on back with antigen in complete Freunds adjuvant (500 μg antigen per rabbit). The rabbits were boosted with same antigen in incomplete Freund adjuvant (250 μg antigen per rabbit) every three weeks. After the fifth boost, the bleeds were collected. The sera were purified by Protein A-sepharose affinity chromatography as previously described (see ANTIBODIES: A LABORATORY MANUAL, Cold Spring Harbor, supra.). Further purification steps were performed using adsorption of specific material to phosphopeptide and nonphosphopeptide affinity columns, followed by elution of reactive material at low pH, as follows. The protein A-purified immunoglobulins were loaded onto a SNSDGI*SPKRRRL—resin column. The bound antibodies were eluted at low pH, collected, and applied onto a SNSDG-ISPKRRRL—resin column. The flow through fraction was collected, dialyzed, and kept in storage buffer.

Antibodies were characterized by Western blotting to examine specificity against whole cell extracts, as described in detail below.

Characterization of p-ATR (Ser428) Antibodies Against Phosphorylated ATR in DNA Damaged Cell Lines and Confirmation of In Vivo Phosphorylation of Ser428.

To characterize the polyclonal antibodies raised against the phosphorylated peptide described above, Western blots were performed with RAW 264.7 cells, which were known to give a strong signal transduction response (ATR-p53 pathway) to DNA damage (see *Free Radic. Biol. Med.* 30: 884-94 and *Biochem. J.* 319: 299-305). The cells were either untreated (control) or treated with either UV (50 mJ/cm$^2$, 30 minute recovery) in order to induce DNA damage and stimulate ATR activity, or Nocadazole (50 ng/mL, 16 hours) in order to arrest cells in metaphase of mitosis. Total ATR was detecting using a total ATR-specific antibody (Novus Biologicals cat# NB 100-322).

FIG. 3 shows the specific detection of human ATR (phosphorylated at Ser428) by the ATR(Ser428) phospho-specific antibody of the invention. Basal phospho-ATR in untreated cells is detected (lane 1), and increase in phosphorylated ATR is detected following UV treatment (lane 2), but not following Nocadazole treatment (lane 3). Analysis of total ATR protein served as a control to indicate equal loading and to verify that the stimuli applied worked as expected. These results confirm that the novel serine 428 ATR phosphorylation site disclosed herein is, in fact, phosphorylated in vivo.

Characterization of p-ATR (Ser428) Antibodies Using ATR Substitution Mutants.

To further examine the specificity of phospho-ATR (Ser428) antibodies, expression constructs encoding epitope (HA) tagged wild-type ATR protein, or ATR containing an amino acid substitution at position 428 (for example serine-to-alanine) in the human sequence may be prepared by transfecting NIH 3T3 cells, according to standard methods (See Qiagen Polyfect® Transfection Reagent Handbook, September 2000).

Transfected cells may be UV treated to induce DNA damage, and hence ATR activation, and HA-ATR proteins may be immunoprecipitated using an anti-HA antibody. The immunoprecipitated material is then immunoblotted using a phospho-ATR(Ser428) antibody. This analysis is useful to further confirm that a phospho-ATR (Ser428) antibody will detect the wild-type ATR protein, but not the mutant ATR having the Ser428 substitution. Anti-HA antibodies are used to control for the amounts of total ATR protein immunoprecipitated and immunoblotted in this type of experiment, and a total ATR immunoblot is used to indicate that the UV treatment worked as expected leading to activation, and hence phosphorylation, of ATR.

Example 2

Production of a Human ATR (Ser2317) Phospho-Specific Antibody

A previously unknown ATR phosphorylation site, serine 2317, was identified as described above by predictive analysis of the human ATR protein sequence using the ScanSite program. Yaffe et al., supra. A 13 amino acid phospho-peptide antigen, ISLKG*SDGKFY (SEQ ID NO: 6) (where *S=phosphoserine), corresponding to residues 2312-2322 of human ATR (see SEQ ID NO: 1; FIG. 1), was constructed according to standard synthesis techniques using a Rainin/Protein Technologies, Inc., Symphony peptide synthesizer. See ANTIBODIES: A LABORATORY MANUAL, supra.; Merrifield, supra. This peptide antigen also corresponds to a highly homologous site in murine ATR (see FIG. 2; SEQ ID NO: 2).

This peptide was coupled to KLH, and rabbits were injected intradermally (ID) on back with antigen in complete Freunds adjuvant (500 μg antigen per rabbit). The rabbits were boosted with same antigen in incomplete Freund adjuvant (250 μg antigen per rabbit) every three weeks. After the fifth boost, the bleeds were collected. The sera were purified by Protein A-sepharose affinity chromatography as previously described (see ANTIBODIES: A LABORATORY MANUAL, Cold Spring Harbor, supra.). Further purification steps were performed using adsorption of specific material to phosphopeptide and nonphosphopeptide affinity columns, followed by elution of reactive material at low pH, as follows. The protein A-purified immunoglobulins were loaded onto a ISLKG*SDGKFY—resin Knotes column. The bound antibodies were eluted at low pH, collected, and applied onto a ISLKGSDGKFY—resin column. The flow through fraction was collected, dialyzed, and kept in storage buffer.

Antibodies were characterized by Western blotting to examine specificity against whole cell extracts, as described in detail below.
Characterization of p-ATR (Ser2317) Antibodies Against Phosphorylated ATR in DNA Damaged Cell Lines and Confirmation of In Vivo Phosphorylation of Ser2317.

To characterize the polyclonal antibodies raised against the phosphorylated peptide described above, Western blots were performed with 264.7 cells, which were known to give a strong signal transduction response (ATR-p53 pathway) to DNA damage (see Free Radic. Biol. Med. 30: supra.) The cells were either untreated (control) or treated with either UV (50 mJ/cm², 30 minute recovery) in order to induce DNA damage and stimulate ATR activity, or Nocadazole (50 ng/mL, 16 hours) in order to arrest cells in metaphase of mitosis. Total ATR was detecting using a total ATR-specific antibody (Novus Biologicals cat# NB 100-322).

FIG. 3 shows the specific detection of human ATR (phosphorylated at Ser2317) by the ATR(Ser2317) phospho-specific antibody of the invention. Basal phospho-ATR is untreated cells is detected (lane 1), and increase in phosphorylated ATR is detected following nocodazole-block (lane 3), but not following UV-treatment (lane 2). Analysis of total ATR protein served as a control to indicate equal loading and to verify that the stimuli applied worked as expected. These results confirm that the novel serine 2317 ATR phosphorylation site disclosed herein is, in fact, phosphorylated in vivo. Characterization of p-ATR (Ser2317) Antibodies Using ATR Substitution Mutants.

To further examine the specificity of phospho-ATR (Ser2317) antibodies, expression constructs encoding epitope (HA) tagged wild-type ATR protein, or ATR containing an amino acid substitution at position 2317 (for example serine-to-alanine) in the human sequence may be prepared by transfecting NIH 3T3 cells, according to standard methods (See Qiagen Polyfect® Transfection Reagent Handbook, September 2000).

Transfected cells may be UV treated to induce DNA damage, and hence ATR activation, and HA-ATR proteins may be immunoprecipitated using an anti-HA antibody. The immunoprecipitated material is then immunoblotted using a phospho-ATR(Ser2317) antibody. This analysis is useful to further confirm that a phospho-ATR (Ser2317) antibody will detect the wild-type ATR protein, but not the mutant ATR having the Ser2317 substitution. Anti-HA antibodies are used to control for the amounts of total ATR protein immunoprecipitated and immunoblotted in this type of experiment, and a total ATR immunoblot is used to indicate that the UV treatment worked as expected leading to activation, and hence phosphorylation, of ATR.

Example 3

Production of a Human ATR (Ser428, Ser2317) Phospho-Specific Monoclonal Antibody Phospho-ATR (Ser428 or Ser2317)—specific monoclonal antibodies may be produced from spleen cells of the immunized BALB/c mice described in Examples 1 and 2, above, following standard procedures (Harlow and Lane, 1988). Briefly, the mouse spleen is fused to SP2/0 mouse myeloma fusion partner cells according to the protocol of Kohler and Milstein (1975). Colonies originating from the fusion are screened by ELISA for reactivity to the phospho-peptide and non-phospho-peptide and by Western blot analysis. Colonies found to be positive by ELISA to the phospho-peptide while negative to the non-phospho-peptide may be further characterized by Western blot analysis. Colonies found to be positive by Western blot analysis are then subcloned by limited dilution. Mouse ascites are produced from positive clones obtained from subcloning. Clones are selected for phospho-specificity by ELISA and by Western blot analysis using cell culture supernatant. Selected positive clones are then subcloned to produce final desired clones producing phospho-ATR (Ser428, Ser2317)-specific monoclonal antibodies.

Ascites fluid from clones obtained from the ATR fusion may be further tested by Western blot analysis. The ascites fluid will likely give similar results on Western blot analysis as observed with the cell culture supernatant, indicating phospho-specificity on ATR-induced 3T3L1 adipocytes and/or L6 differentiated myocyte cells, for example.

Example 4

Production and Use of AQUA Peptides for the Quantification of ATR (Ser428, Ser2317) Protein Phosphorylation Heavy-isotope labeled peptides (AQUA peptides (internal standards)) for the detection and quantification of ATR kinase only when phosphorylated at Ser428 and/or Ser2317 are produced according to the standard AQUA methodology (see Gygi et al., Gerber et al., supra.) methods by first constructing a synthetic peptide standard corresponding to the respective phosphorylation site sequence (see FIG. 1, underlines) and incorporating a heavy-isotope label. Subsequently, the MS"

and LC-SRM signature of the peptide standard is validated, and the AQUA peptide is used to quantify native peptide in a biological sample, such as a digested cell extract. Production and use of exemplary AQUA peptides is provided below.

ATR (Serine 428).

An AQUA peptide comprising the sequence, NLSSNSDGIs*PKRRRLSSSLNPSKRAPKQTE (s*=phosphoserine; sequence incorporating $^{14}C/^{15}N$-labeled proline (indicated by bold P) (SEQ ID NO: 7), which corresponds to the serine 428 phosphorylation site in human ATR kinase (see FIG. 1 (SEQ ID NO: 1), residues 419-449), is constructed according to standard synthesis techniques using, e.g., a Rainin/Protein Technologies, Inc., Symphony peptide synthesizer (see Merrifield, supra.) as further described below in Synthesis & MS/MS Signature. This ATR peptide corresponds to a predicted GluC digest fragment. The ATR (Ser428) AQUA peptide is then spiked into a biological sample to quantify the amount of phosphorylated ATR (Ser428) in the sample, as further described below in Analysis & Quantification.

ATR (Serine 2317).

An AQUA peptide comprising the sequence DMVEILASLQKPKKISLKGs*DGKFYIMMCKPK (s*=phosphoserine; sequence incorporating $^{14}C/^{15}N$-labeled proline (indicated by bold P) (SEQ ID NO: 8), which corresponds to the serine 2317 phosphorylation site in human ATR kinase (see FIG. 1 (SEQ ID NO: 1), residues 2298-2329), is constructed according to standard synthesis techniques using, e.g., a Rainin/Protein Technologies, Inc., Symphony peptide synthesizer (see Merrifield, supra.) as further described below in Synthesis & MS/MS Signature. This ATR peptide corresponds to a predicted AspN digestion fragment. The ATR(Ser2317) AQUA peptide is then spiked into a biological sample to quantify the amount of phosphorylated ATR (Ser2317) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif.). Fmoc-derivatized stable-isotope monomers containing one $^{15}N$ and five to nine $^{13}C$ atoms may be obtained from Cambridge Isotope Laboratories (Andover, Mass.). Preloaded Wang resins may be obtained from Applied Biosystems. Synthesis scales may vary from 5 to 25 μmol. Amino acids are activated in situ with 1-H-benzotriazolium, 1-bis (dimethylamino) methylene]-hexafluorophosphate (1-),3-oxide: 1-hydroxybenzotriazole hydrate and coupled at a 5-fold molar excess over peptide. Each coupling cycle is followed by capping with acetic anhydride to avoid accumulation of one-residue deletion peptide by-products. After synthesis peptide-resins are treated with a standard scavenger-containing trifluoroacetic acid (TFA)-water cleavage solution, and the peptides are precipitated by addition to cold ether. Peptides (i.e. a desired ATR AQUA peptide described above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (phosphorylated ATR kinase) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LCQ DecaXP ion trap or TSQ Quantum triple quadrupole). On the DecaXP, parent ions are isolated at 1.6 m/z width, the ion injection time being limited to 150 ms per microscan, with two microscans per peptide averaged, and with an AGC setting of $1 \times 10^8$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated antibody that binds to human Ataxia-Telangiectasia and Rad3-related (ATR) kinase when phosphorylated at serine 428 (SEQ ID NO: 1), but does not bind human ATR when not phosphorylated at serine 428 (SEQ ID NO: 1).

2. The antibody of claim 1, wherein said antibody is polyclonal.

3. The antibody of claim 1, wherein said antibody is monoclonal.

4. An immortalized cell line producing the antibody of claim 3.

5. A kit for detection of phosphorylated ATR (Ser428) in a biological sample, said kit comprising at least one detectable antibody of claim 1.

6. A method for detecting phosphorylated ATR kinase in a biological sample, said method comprising the steps of:
 (a) contacting a biological sample potentially, or suspected of, containing phosphorylated ATR kinase with at least one detectable antibody that binds to human Ataxia-Telangiectasia and Rad3-related (ATR) kinase when phosphorylated at serine 428 (SEQ ID NO: 1), but does not bind human ATR when not phosphorylated at serine 428 (SEQ ID NO: 1), under conditions suitable for formation of an antibody-ATR kinase complex; and
 (b) detecting the presence of said complex in said sample, wherein the presence of said complex indicates the presence of phosphorylated ATR kinase in said sample.

* * * * *